US009464754B1

United States Patent
Troy et al.

(10) Patent No.: US 9,464,754 B1
(45) Date of Patent: Oct. 11, 2016

(54) AUTOMATED MOBILE BOOM SYSTEM FOR CRAWLING ROBOTS

(71) Applicant: The Boeing Company, Chicago, IL (US)

(72) Inventors: James J. Troy, Issaquah, WA (US); Scott W. Lea, Renton, WA (US); Gary E. Georgeson, Tacoma, WA (US); Karl Edward Nelson, Shoreline, WA (US); Daniel James Wright, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/181,516

(22) Filed: Jun. 14, 2016

Related U.S. Application Data

(62) Division of application No. 14/176,169, filed on Feb. 10, 2014, now Pat. No. 9,410,659.

(51) Int. Cl.
*G06F 19/00* (2011.01)
*F16M 11/18* (2006.01)
*F16M 11/42* (2006.01)
(Continued)

(52) U.S. Cl.
CPC .............. *F16M 11/18* (2013.01); *F16M 11/42* (2013.01); *G01N 29/225* (2013.01); *G01N 29/265* (2013.01); *G01N 29/28* (2013.01); *G05D 1/0276* (2013.01); *G05D 2201/0207* (2013.01); *Y10S 901/01* (2013.01)

(58) Field of Classification Search
CPC .... F16M 11/18; F16M 11/42; G01N 29/225; G01N 29/265; G01N 29/28; G05D 1/0276
See application file for complete search history.

(56) References Cited

U.S. PATENT DOCUMENTS

| 6,752,541 B1 | 6/2004 | Dykyj |
| 7,194,358 B2 | 3/2007 | Callaghan et al. |

(Continued)

FOREIGN PATENT DOCUMENTS

| EP | 1721213 B1 | 4/2013 |
| WO | 2013019301 A1 | 2/2013 |

OTHER PUBLICATIONS

Invitation to Pay with Partial International Search Report, International Application No. PCT/US2014/062338 (foreign counterpart of the parent of the instant U.S. patent application), dated Feb. 12, 2015.

*Primary Examiner* — Ian Jen
(74) *Attorney, Agent, or Firm* — Ostrager Chong Flaherty & Broitman P.C.

(57) ABSTRACT

A system comprising a multi-functional boom subsystem integrated with a holonomic-motion boom base platform. The boom base platform may comprise: Mecanum wheels with independently controlled motors; a pair of sub-platforms coupled by a roll-axis pivot to maintain four-wheel contact with the ground surface; and twist reduction mechanisms to minimize any yaw-axis twisting torque exerted on the roll-axis pivot. A computer with motion control software may be embedded on the boom base platform. The motion control function can be integrated with a real-time tracking system. The motion control computer may have multiple platform motion control modes: (1) a path following mode in which the boom base platform matches the motion path of the surface crawler (i.e., integration with crawler control); (2) a reactive mode in which the boom base platform moves based on the pan and tilt angles of the boom arm; and (3) a collision avoidance mode using sensors distributed around the perimeter of the boom base platform to detect obstacles.

20 Claims, 13 Drawing Sheets

(51) Int. Cl.
 *G05D 1/02* (2006.01)
 *G01N 29/22* (2006.01)
 *G01N 29/265* (2006.01)
 *G01N 29/28* (2006.01)
(52) U.S. Cl.

(56) References Cited

U.S. PATENT DOCUMENTS 7,643,893 B2  1/2010 Troy et al.
8,333,520 B1  12/2012 Cronin et al.
8,713,998 B2  5/2014 Troy et al.
8,738,226 B2  5/2014 Troy et al.
9,010,684 B2  4/2015 Motzer et al.
9,043,146 B2  5/2015 Troy et al.
2014/0267778 A1* 9/2014 Webb .................. H04N 5/2328
                                                          348/169
2014/0278221 A1  9/2014 Troy et al.
2015/0226369 A1* 8/2015 Troy ..................... F16M 11/18
                                                          180/2.1

* cited by examiner

AUTOMATED MOBILE BOOM SYSTEM FOR CRAWLING ROBOTS

RELATED PATENT APPLICATIONS

This application is a divisional of and claims priority from U.S. patent application Ser. No. 14/176,169 filed on Feb. 10, 2014. In addition, the disclosures of the following patents and published patent application are incorporated by reference herein in their respective entireties: U.S. Pat. No. 7,194,358 issued on Mar. 20, 2007; U.S. Pat. No. 7,643,893 issued on Jan. 5, 2010; U.S. Pat. No. 8,713,998 issued on May 6, 2014; U.S. Pat. No. 8,738,226 issued on May 27, 2014; U.S. Pat. No. 9,043,146 issued on May 26, 2015; and U.S. Patent Application Publ. No. 2014/0278221 published on Sep. 18, 2014.

BACKGROUND

This disclosure generally relates to systems for managing the take-up and pay-out of long flexible objects such as cables, ropes and hoses. For the purpose of illustration, systems for managing the take-up and pay-out of umbilical cables for crawling robots will be described.

When using robotic surface-crawling vehicles (hereinafter "robotic crawlers") in maintenance (e.g., inspection) applications, power and control signals need to be sent to the robotic crawler, and data from on-board sensors, such as non-destructive inspection (NDI) equipment, needs to be sent from the robotic crawler to a command center. In most applications this power and data transfer is handled by an umbilical cable. The umbilical cable may also include a hose that supplies water to the robotic crawler in cases where the NDI equipment comprises one or more ultrasonic transducer arrays that use water as acoustic couplant. The umbilical cable is often heavier than the robotic crawler, which can disrupt the motion of the crawler if the cable weight tension is not relieved, and extra cable length must be kept far enough away from the robotic crawler to avoid entanglements.

Umbilical cable management for robotic crawlers usually involves some type of overhead gantry and track-based system. These can be large and difficult to install in the field and are usually feasible only in fixed locations. Standard ground-based vehicles, like boom-trucks or scissor lifts, have also been used as platforms for cable management, but due to the limited mobility of these types of platforms, they may be unsuitable for use with general-purpose robotic crawlers that have large ranges of motion.

An alternative solution is to use wireless data transmission and on-board power, but that approach has other types of limitations, including: length of time on target, wireless bandwidth, and wireless restrictions in some areas.

In addition, when the robotic crawler is used in situations where it may fall off the target object undergoing maintenance (e.g., inspection), the system should have a fall protection system. One class of fall protection devices for robotic crawlers is safety nets. Nets may work in some situations, but require significant support infrastructure and may be difficult to set up in a manner that provides the desired coverage. Another class of fall protection devices for robotic crawlers is safety tether cables. In some implementations, this safety tether cable may be combined with the power-data umbilical cable. Fall protection systems are currently available for humans, which include: cables and safety lines paid out from overhead superstructure on a building or moved around the object being inspected (e.g., an airplane); and booms with cables and safety lines extended off high lift equipment or other factory equipment.

In order to facilitate the use of remotely operated tool-equipped robotic crawlers, a system for efficiently managing an umbilical cable and protecting the robotic crawler and the environment from fall events is desired.

SUMMARY

Control of a safety tether-power-data umbilical cable, having a distal end connected to a robotic crawler, requires support equipment capable of bearing the weight of the cable as well as the weight of the robotic crawler in the event the latter falls from a target object. The support equipment should also allow free motion of the robotic crawler, while sensing conditions that indicate a crawler fall, and then respond appropriately. The support equipment should also be capable of moving in such a way as to properly follow the robotic crawler, while avoiding collisions with objects that may be in its environment. In accordance with the teachings disclosed herein, systems can be designed which have all of the foregoing capabilities. These systems comprise a customizable boom integrated with a holonomic-motion base platform.

A holonomic system is one that is not subject to motion constraints. As used in this disclosure, a vehicle is considered to be holonomic if the controllable degrees of freedom are equal to the total degrees of freedom. This type of system can translate in any direction while simultaneously rotating. This is different than most types of ground vehicles, such as car-like vehicles, tracked vehicles, or wheeled differential-steer (skid-steer) vehicles, which cannot translate in any direction while rotating at the same time.

In accordance with embodiments disclosed herein, a multi-functional boom subsystem is provided that may include some or all of the following features: a boom arm having a hollow center for umbilical cable travel; a two-axis gimbal with angle sensors for detecting the pan and tilt angles of the boom arm; an electrically controlled boom arm fall arrest mechanism; motorized control of cable pay-out; automated motorized control of counterweight for balancing the boom arm; the ability to add or remove extension sections of the boom arm to provide customized length adjustment; and an extendable vertical stanchion.

In accordance with some embodiments disclosed herein, a holonomic-motion boom base platform is provided that may include some or all of the following features: Mecanum wheels with independently controlled motors to allow motion in any direction; a roll-axis pivot to maintain four-wheel contact with the ground surface and allow the base platform to crawl over non-planar surfaces, small step height changes, hoses, wires, etc.; and twist reduction mechanisms to minimize any yaw-axis twisting torque exerted on the roll-axis pivot.

A computer with motion control software may be embedded on the boom base platform. The motion control function can be integrated with a real-time tracking system. In accordance with one embodiment, the motion control computer has multiple platform motion control modes: (1) a path following mode in which the boom base platform matches the motion path of the surface crawler (i.e., integration with crawler control); (2) a reactive mode in which the boom base platform moves based on the pan and tilt angles of the boom arm; and (3) a collision avoidance mode using sensors distributed around the perimeter of the boom base platform to detect obstacles.

In accordance with some embodiments, the automated cable management and fall protection system for managing umbilical cables of robotic crawlers enables wide-area coverage of a target object by a robotic crawler by controlling the position and orientation of a holonomic-motion boom base platform, while simultaneously measuring boom arm gimbal angles, counterweight position, and umbilical cable feed. The system adaptively maintains the position of the end of the boom arm in proximity to the robotic crawler to provide sufficient slack in the umbilical cable while the robotic crawler is moving around on the target surface, and in the event that the robotic crawler falls from the target object, the system tensions the cable and resists rotation of the gimbal about the tilt axis to slow the fall of the robotic crawler. Two separate types of automated control will be disclosed: one using an external tracking system and another using on-board sensors.

One aspect of the subject matter disclosed in detail below is a mobile boom system comprising: a mobile boom base platform; a rotary mast carried by the boom base platform and rotatable relative to the boom base platform about a pan axis; a gimbal comprising a first portion attached to the rotary mast and a second portion rotatable relative to the rotary mast about a tilt axis; a boom arm having first and second ends and an intermediate portion coupled to the gimbal, the boom arm having a hollow center; a tilt angle sensor for detecting a tilt angle of the boom arm; at least one counterweight supported on a portion of the boom arm disposed between the intermediate portion and the first end; a counterweight positioning subsystem for changing the a position of the at least one counterweight relative to the gimbal; and a computer system programmed to receive tilt angle data from the tilt angle sensor and send control signals to the counterweight positioning subsystem for controlling the position of the at least one counterweight as a function of at least the tilt angle data. The foregoing system may further comprise: a pay-out/take-up subsystem disposed near the first end of the boom arm; a cable extending from the pay-out/take-up subsystem through the hollow center of the boom arm; and a robotic crawler attached to a distal end of the cable, the computer system being further programmed to control movement of the robotic crawler on a surface by means of signals communicated to the robotic crawler via the umbilical cable and control pay-out and take-up of the cable as a function of the tilt angle data.

Another aspect of the subject matter disclosed herein is a holonomic-motion platform comprising: first and second sub-platforms; first and second wheels rotatably coupled to the first sub-platform; third and fourth wheels rotatably coupled to the second sub-platform; and a roll-axis pivot rod comprising first and second portions respectively coupled to the first and second sub-platforms, wherein the first sub-platform is rotatably coupled to the roll-axis pivot rod, and each of the first through fourth wheels comprises a respective plurality of rollers rotatably mounted along a circumference. The foregoing holonomic-motion boom base platform may further comprise first and second yaw-axis twist reduction rollers disposed on opposing sides of the roll-axis pivot rod, each of the first and second yaw-axis twist reduction rollers being rotatably coupled to one of the first and second sub-platforms and bearing against the other of the first and second sub-platforms.

A further aspect is a mobile boom system comprising: a self-propellable mobile boom base platform comprising a plurality of rolling elements and a plurality of motors respectively coupled to the plurality of rolling elements; a rotary mast carried by the boom base platform and rotatable relative to the boom base platform about a pan axis; a gimbal comprising a first portion attached to the rotary mast and a second portion rotatable relative to the rotary mast about a tilt axis; a hollow boom arm having first and second ends and an intermediate portion coupled to the gimbal; a cable extending through the hollow boom arm; a pan angle sensor for detecting a pan angle of the boom arm; and a computer system programmed to receive pan angle data from the pan angle sensor and send control signals to the motors for changing the position of the boom base platform as a function of at least the pan angle data. In one embodiment, the computer system is programmed to cause the boom base platform to move when the pan angle of the boom arm reaches a specified threshold pan angle.

Yet another aspect of the subject matter disclosed herein is a mobile boom system comprising: a mobile boom base platform; a rotary mast carried by the boom base platform and rotatable relative to the boom base platform about a pan axis; a gimbal comprising a first portion attached to the rotary mast and a second portion rotatable relative to the rotary mast about a tilt axis; a boom arm having first and second ends and an intermediate portion coupled to the gimbal, the boom arm having a hollow center; a cable extending through the hollow boom arm; a robotic crawler attached to a distal end of the cable; an electrically controlled boom arm fall arrest mechanism having first and second ends respectively coupled to the boom arm and the rotary mast; a tilt angle sensor for detecting a tilt angle of the boom arm; and a computer system programmed to monitor the output of the tilt angle sensor and issue a fall arrest trigger signal to the boom arm fall arrest mechanism in response to a rate of rotation of the boom arm about the tilt axis exceeding a specified threshold.

The automated mobile boom systems disclosed herein solve the problem of providing automated cable management and fall protection while not restricting robotic crawler movement within the activity space for robots and humans working above the ground. Without this system, either a person is needed to monitor the boom and adjust the cable as the robotic crawler moves, or the crawler usage is restricted to very small inspection areas. The solution presented here addresses general-purpose cable management for robotic crawlers working high off the ground along horizontal and vertical surfaces, and it supports relatively long and moderately heavy umbilical cables. Methods of collision avoidance of the cable management platform with objects in its environment are also provided.

Other aspects are disclosed in the detailed description that follows.

BRIEF DESCRIPTION OF THE DRAWINGS

Reference will hereinafter be made to the drawings in which similar elements in different drawings bear the same reference numerals.

DETAILED DESCRIPTION

Various embodiments of a mobile boom system will now be described in detail for purposes of illustration only. These mobile boom systems are configured and programmed to perform various automated functions, including cable management and crawler fall protection. Each system disclosed in detail below comprises a boom integrated with a holonomic-motion base platform that is capable of simultaneous rotation and translation in any direction on a surface. Although the disclosed embodiments comprise systems for managing umbilical cables of robotic crawlers, they may also be adapted for use in managing cables, ropes, or hoses for non-robotic systems and for human operators.

Figure 1:
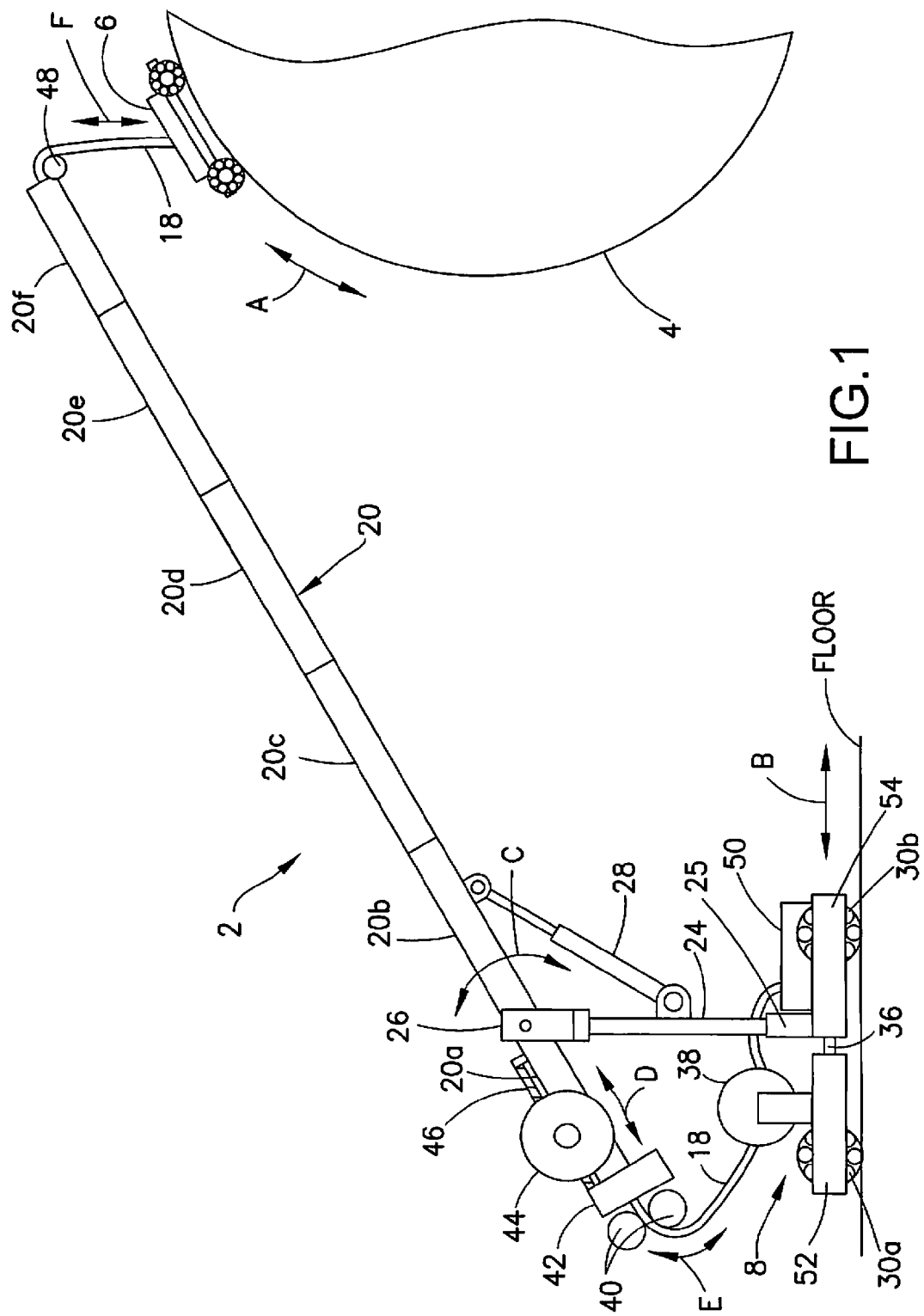
FIG. 1 is a diagram representing an elevational view showing the configuration of a mobile boom system for managing an umbilical cable in accordance with one embodiment.

FIG. 1 shows a configuration of a mobile boom system for managing an umbilical cable 18 in accordance with one embodiment. The umbilical cable 18 is connected to a robotic crawler 6 located on a surface of a target object 4 (e.g., an airplane). The robotic crawler 6 may be a holonomic-motion robotic crawler capable of motion in any direction on a surface. As one example, the double-headed arrow A in FIG. 1 represents motion of the robotic crawler 6 along the surface of target object 4. The robotic crawler may comprise Mecanum wheels for enabling holonomic motion and suction zones for holding the robotic crawler against a vertical surface, as disclosed in U.S. Pat. No. 8,738,226.

The mobile boom system depicted in FIG. 1 comprises a multi-function boom subsystem 2 mounted on a holonomic-motion boom base platform 8, i.e., the boom base platform 8 is also capable of motion in any direction. For example, the double-headed arrow B represents motion of the base platform 8 along a floor.

Figure 8:
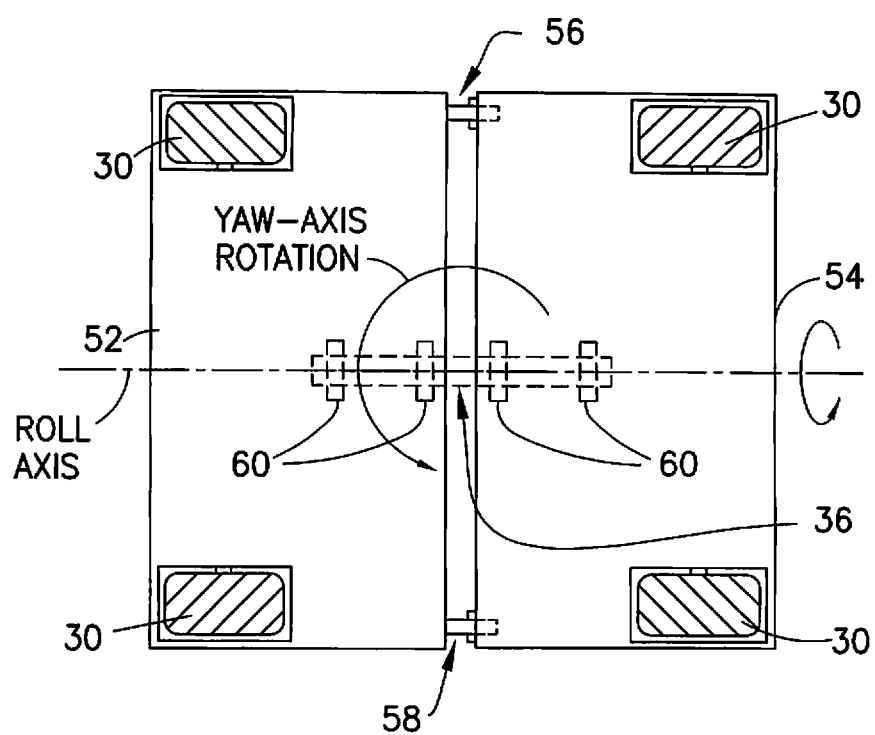
FIG. 8 is a diagram representing a top view of a holonomic-motion base platform having a roll axis pivot and twist reduction rollers.

The boom base platform 8 may comprise a pair of sub-platforms 52 and 54 coupled by a roll-axis pivot rod 36 (explained in more detail later with reference to FIGS. 8 and 9). Each sub-platform 52, 54 has a respective pair of Mecanum wheels 30 (only one Mecanum wheel of each pair is visible in FIG. 1) rotatably mounted thereto. The boom base platform 8 can be made to move in any direction and turn by varying the speed and direction of rotation of each wheel.

The boom base platform 8 further comprises a mast base 25 rigidly attached to the sub-platform 54 and a rotary mast 24 rotatably coupled to the mast base 25. The mast base 25 projects above the sub-platform 54 as seen in FIG. 1. The rotary mast 24 may take the form of a vertical stanchion which is rotatably coupled to the mast base 25 by bearings (not shown) for rotation about a pan axis (coaxial with its own axis). The rotary mast 24 is removable from the support mast base 25 for transport.

In accordance with the embodiment shown in FIG. 1, a tension reel 38 is mounted on sub-platform 52. (The tension reel is not shown in FIG. 3.) A portion of the umbilical cable 18 is wound on the tension reel 38. In addition, an electrical subsystem 50 (comprising electronics, controller hardware and an embedded personal computer) is mounted on sub-platform 54. The electrical subsystem 50 provides power to the motors incorporated in boom subsystem 2, robotic crawler 6, and boom base platform 8 (which motors are identified in FIG. 10, to be discussed later).

The boom subsystem 2 is carried by the boom base platform 8. The boom subsystem 2 comprises a boom arm 20 in the form of a hollow tube having a channel for travel of a portion of the umbilical cable 18, which has a length greater than the length of the boom arm 20. In the embodiment depicted in FIG. 1, the boom arm 20 comprises a multiplicity of cylindrical boom arm segments 20a-20f made of a strong, light-weight material (e.g. carbon fiber), which are connected in series. Segmented construction of the boom arm 20 gives the technician the ability to add or remove extension sections to provide customized length adjustment. A paid-out portion of the umbilical cable 18 travels in the channel of the boom arm 20.

Still referring to FIG. 1, an intermediate portion of the boom arm 20 is attached to a gimbal 26, which is in turn attached to an upper end of the rotary mast 24. The rotary mast 24 may be constructed from vertical segments which can be added or removed to adjust the height of gimbal 26 above the floor. The gimbal 26 and the boom arm 20, being mounted to the rotary mast 24, are also rotatable about the pan axis. In addition, the gimbal 26 enables the boom arm 20 to rotate about a tilt axis of the gimbal 26. Rotational encoders (not shown in FIG. 1, but see FIG. 10) are respectively attached to the rotary mast 24 and the gimbal 26 to measure the pan and tilt angles of the boom arm 20. This configuration allows the boom arm 20 to swing freely about pan and tilt axes relative to boom base platform 8.

The boom subsystem 2 depicted in FIG. 1 may further comprise components for performing multiple additional functions, including but not limited to umbilical cable management, real-time angle sensing, equilibrium balancing, and fall arrest, as explained in detail below.

Umbilical Cable Management

Still referring to FIG. 1, the umbilical cable 18 can be extended or retracted using a pair of cable rollers 40 which pinch the umbilical cable 18 adjacent a proximal end of boom arm 20. The cable rollers 40 are driven to rotate (in opposite directions) by a cable motor 42. The umbilical cable 18 passes through the channel of boom arm 20 and exits boom arm 20 at a distal end thereof. The exiting portion of the umbilical cable 18 is guided by a passive cable guide pulley 48, which is mounted to the distal end of boom arm 20. Preferably, the portion of the umbilical cable 18 disposed between the robotic crawler 6 and the cable guide pulley 48 may have an amount of slack. That portion of the umbilical cable 18 moves up or down, as indicated by double-headed arrow F in FIG. 1, as the umbilical cable 18 is retracted or extended respectively, as indicated by double-headed arrow E in FIG. 1.

During cable retraction/extension, the umbilical cable 18 is pulled/pushed through the hollow tube that makes up the boom arm 20. The umbilical cable 18 is also pulled in an opposite direction by gravity acting on the weight of the robotic crawler 6 and the additional length of the umbilical cable 18 connecting the boom arm 20 to the robotic crawler 6. The motion of the umbilical cable 18 may be automatically extended or retracted by a cable motion control subsystem (which controls the cable motor 42) using feedback from a device that measures the boom arm tilt angle (e.g., a rotational encoder), as described in more detail below. This cable motion is coordinated with the base platform motion (also discussed later). A cable slack can be taken up using the tension reel 38 (or alternatively, allowed to accumulate in a bucket carried by the robotic crawler 6).

Real-Time Angle Sensing

As previously mentioned, the boom arm 20 is pivotally supported by gimbal 26, which in turn is attached to the distal end of rotary mast 24. The gimbal 26 allows the boom arm 20 to rotate about a tilt axis while the rotary mast 24 is rotatable about the pan axis. For example, the double-headed arrow C in FIG. 1 represents rotation of the boom arm 20 about the tilt axis of gimbal 26. The gimbal 26 is provided with a tilt angle sensor, while the support mast 24 is provided with a pan angle sensor, neither sensor being shown in FIG. 1 These angle sensors may take the form of rotational encoders (see, e.g., tilt encoder 16a and pan encoder 16b in FIG. 10).

Equilibrium Balancing

The boom subsystem 2 shown in FIG. 1 further comprises counterweights 44 (only one is visible in FIG. 1) which are movable back and forth along the boom arm 20 (as indicated by double-headed arrow D in FIG. 1) for the purpose of balancing the moments on opposite sides of the gimbal 26 to achieve a boom arm equilibrium position. The counterweights 44 are moved by a motor-driven, non-backdrivable lead screw 46, which holds the weights in place even when power is disrupted. Control of counterweight position is provided either by direct operator commands or by a computer programmed in accordance with an automatic balancing algorithm. The automated position control is based on feedback of the gimbal tilt angle in order to achieve a neutrally balanced boom arm. The counterweight motion rate is sufficient to address static balance or slow changes to the balance point, but it cannot be changed fast enough to stop a falling robotic crawler 6; for that, a separate fall arrest technique is used.

Fall Arrest

The boom subsystem 2 shown in FIG. 1 further comprises a fall arrest system. In order to stop a falling crawler, the fall arrest system monitors the rate of rotation of the boom arm about the tilt axis and if the rate of rotation exceeds preset threshold value, a two-state (on/off) fall arrest damper 28 is engaged, which slows the fall of the robotic crawler 6. In accordance with the embodiment shown in FIG. 3, the fall arrest damper 28 can take the form of an air-filled cylinder having one end coupled to the rotary mast 24 and having a piston coupled to the boom arm 20. The default state of the air-filled cylinder is to be in fluid communication with the ambient atmosphere by way of an electrically controlled valve in an open state. In response to detection of a fall of the robotic crawler 6, the valve is closed so that the air-filled cylinder will provide a resistance to its associated piston for damping the descent of the distal end of the boom arm 20.

Figure 4:
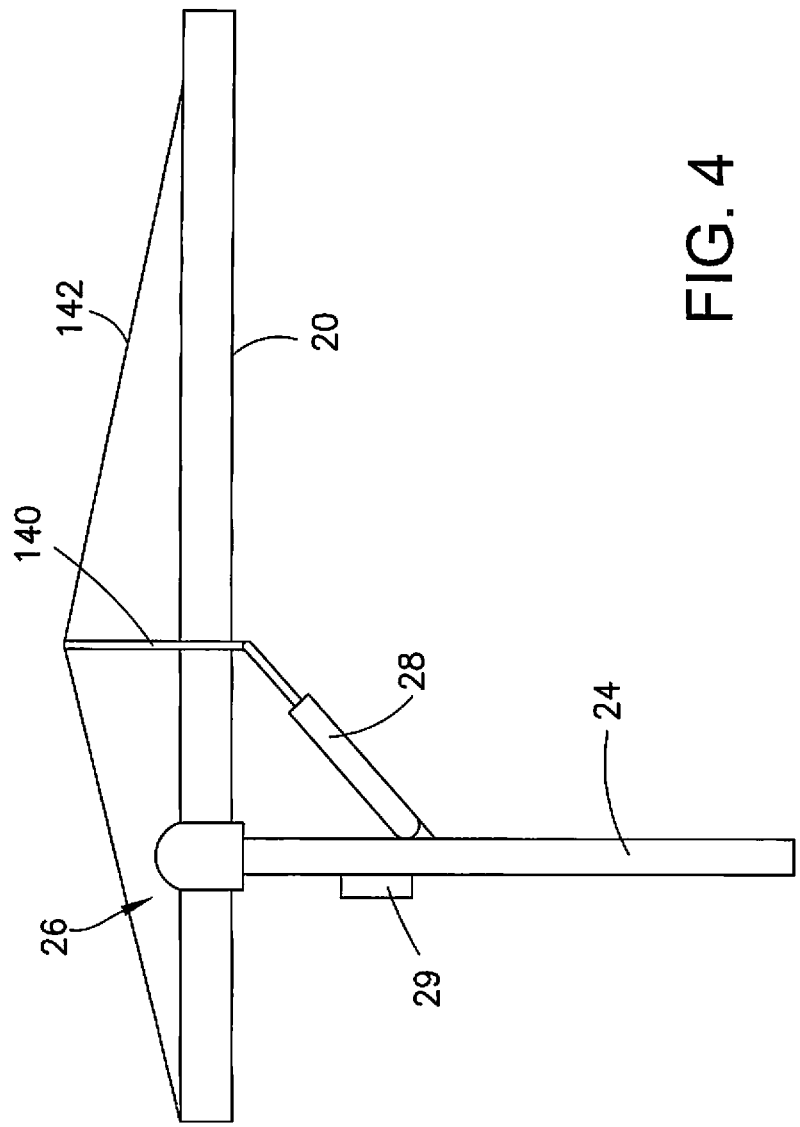
FIG. 4 is a diagram representing an elevational view showing components of a boom arm assembly in accordance with an alternative configuration.

In accordance with the alternative embodiment partly depicted in FIG. 4, the fall arrest damper 28 can take the form of an oil-filled cylinder which is in fluid communication with an oil reservoir 29 that is attached to the rotary mast 24 near the lower mount point of the oil-filled cylinder. Since the oil is incompressible, it stops a falling payload much faster than air does. The system shown in FIG. 4 further comprises a strut 140 (or other rigid element) attached to the boom arm 20 and a guy line 142 connecting a top of strut 140 to opposing portions of the boom arm 20. The piston of the fall arrest damper 28 is coupled to the bottom of strut 140. The guy line 142 increases the load-carrying capacity of the boom arm 20.

Figure 2:
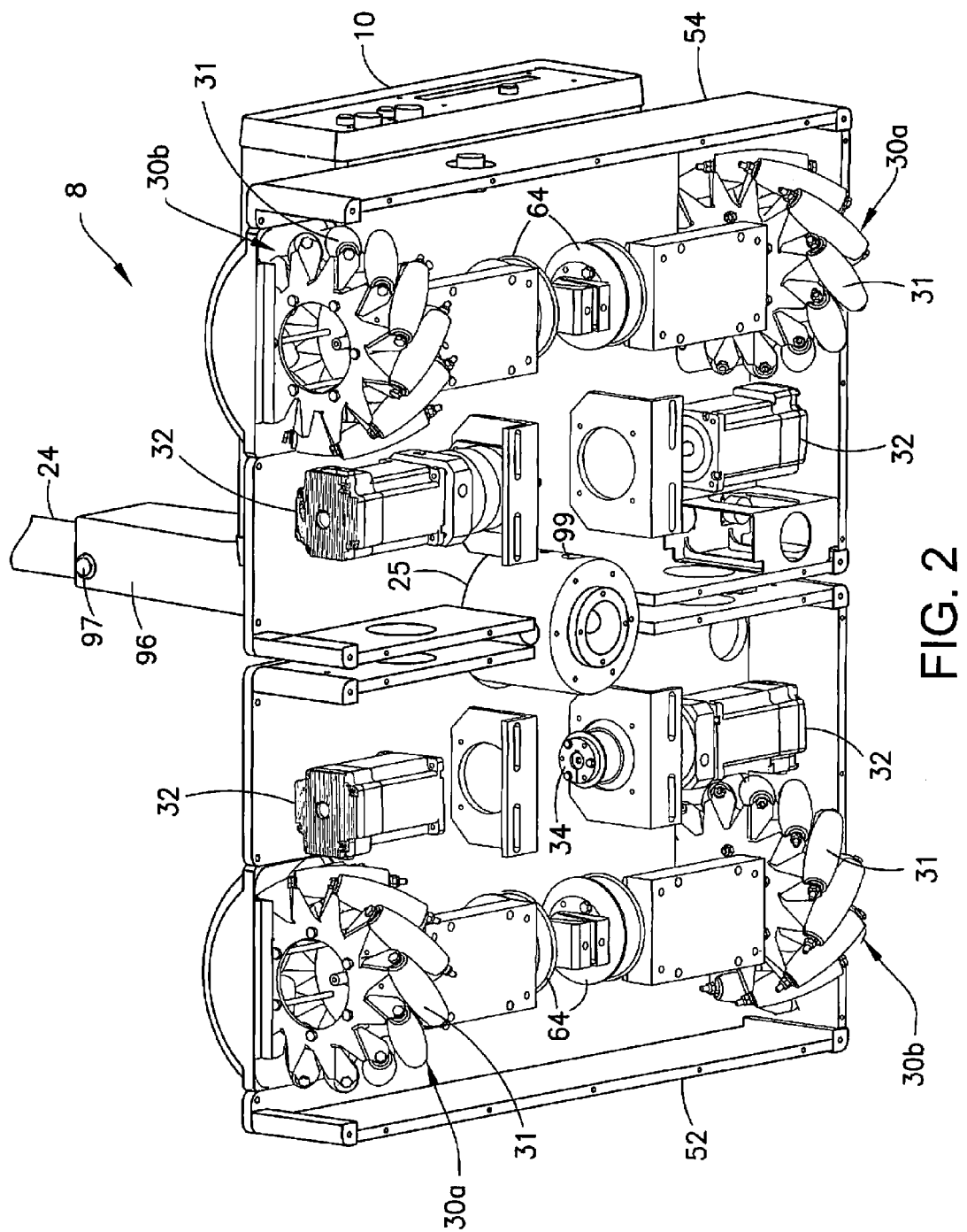
FIG. 2 is a diagram representing an isometric view (from a vantage point below) showing some components of a holonomic-motion boom base platform in accordance with one embodiment.

FIG. 2 shows some components of a holonomic-motion base platform that employs Mecanum wheels. The standard configuration for a Mecanum-wheeled vehicle has four Mecanum wheels (two Type A and two Type B). However, the platform may have any multiple of four Mecanum wheel, e.g., 4, 8, 12, etc. More specifically, as shown in FIG. 2, each of sub-platforms 52 and 54 has a Type A Mecanum wheel 30a and a Type B Mecanum wheel 30b. The Mecanum wheels are arranged with the Type A pair on one diagonal and the Type B pair on the other. The Type A Mecanum wheels 30a differ from the Type B Mecanum wheels 30b in that the tapered rollers 31 of the former are oriented at different angles than the tapered rollers 31 of the latter.

Each Mecanum wheel 30a/30b is driven to rotate by a respective independently controlled stepper motor 32. In the embodiment depicted in FIG. 2, each Mecanum wheel 30a/30b is connected to a respective pulley 64 by means of an axle (not shown in FIG. 2, but see axles 65 in FIG. 9). The pulleys 64 are coupled to respective pulleys 34 (only one of which is depicted in FIG. 2) by respective belts (not shown in FIG. 2), the pulleys 34 being mounted on the output shafts of the stepper motors 32.

A Mecanum-wheeled vehicle can be made to move in any direction and turn by controlling the speed and direction of rotation of each wheel. For example, rotating all four wheels in the same direction at the same rate causes forward or backward movement; rotating the wheels on one side at the same rate but in the opposite direction of the rotation by the wheels on the other side causes the vehicle to rotate; and rotating the Type "A" wheels at the same rate but in the opposite direction of the rotation of the Type "B" wheels causes sideways movement. As seen in FIG. 2, each Mecanum wheel 30 has a multiplicity of tapered rollers 31 rotatably mounted to its circumference, each roller being freely rotatable about its axis. In one embodiment these rollers have an axes of rotation which lie at a 45° angle with respect to the plane of the wheel. The boom base platform 8 can be made to move in any direction and turn by controlling the speed and direction of rotation of the Mecanum wheels 30a/30b.

FIG. 2 also shows that the mast base 25, which is shown in FIG. 1 projecting above the boom base platform 8, extends inside the boom base platform 8 and is attached to sub-platform 54. The rotary mast 24 is coaxial with the mast base 25. The mast base 25 has a diametral hole 99 for receiving a roll-axis pivot (not shown in FIG. 2, but see roll-axis pivot 36 in FIG. 9). In accordance with the embodiment depicted in FIG. 2, an LED tower 96 can be placed around the upwardly projecting portion of the mast base 25, each side of the LED tower 96 having a respective LED 97 for use in conjunction with a local positioning system (LPS) for tracking the whereabouts of the boom base platform 8. The LED-based tracking method uses the LEDs 97 on the base platform along with the LPS to determine the initial position, and then incrementally updates the location with odometry from encoders (not shown). Such an LED-based tracking method is disclosed in U.S. Pat. No. 9,043,146.

Figure 3:
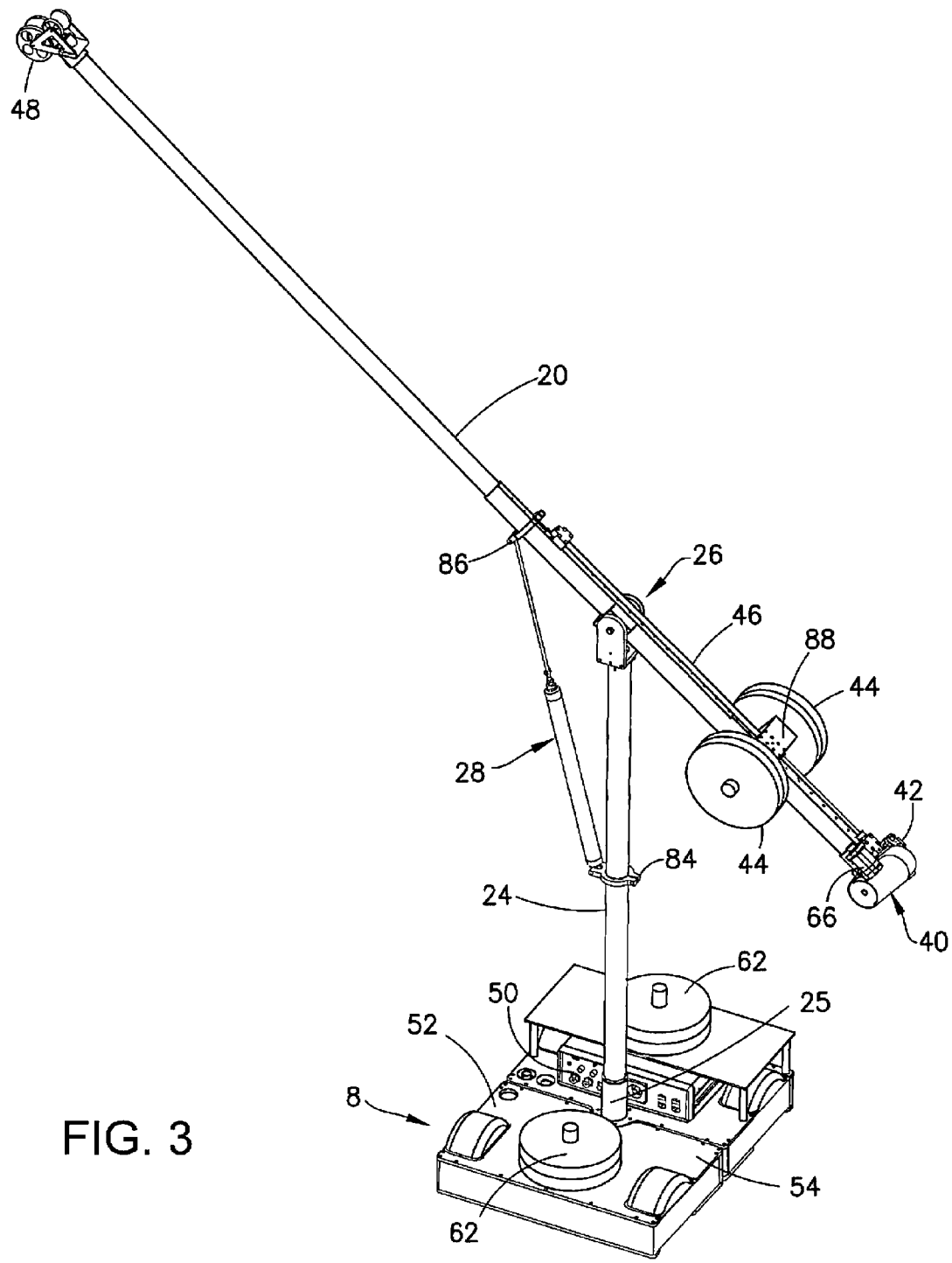
FIG. 3 is a diagram representing an isometric view of a mobile boom system for managing an umbilical cable in accordance with another embodiment.

FIG. 3 depicts a mobile boom system for managing an umbilical cable in accordance with another embodiment. The tension reel for the umbilical cable is not shown. The fall arrest damper 28 comprises a piston/cylinder with one end coupled to an intermediate portion of the rotary mast 24 and the other end coupled to an intermediate portion of the boom arm 20. The boom base platform 8 further comprises ballast disposed inside or on sub-platforms 52 and 54. The weight of the ballast opposes any forces tending to tip or tilt the boom base platform 8. In the implementation shown in FIG. 3, the ballast comprises stacked metal plates 62. In an alternative implementation (not shown), the ballast may comprise containers filled with liquid (e.g., water).

In addition, FIG. 3 shows a pair of counterweights 44 carried by a carriage 88 which is coupled to a lead screw 46. The carriage 88 moves along the boom arm 20 when the lead screw 46 is driven to rotate by a counterweight motor 66. The counterweight subsystem is shown in greater detail in FIGS. 5, 6 and 6A.

Figure 5:
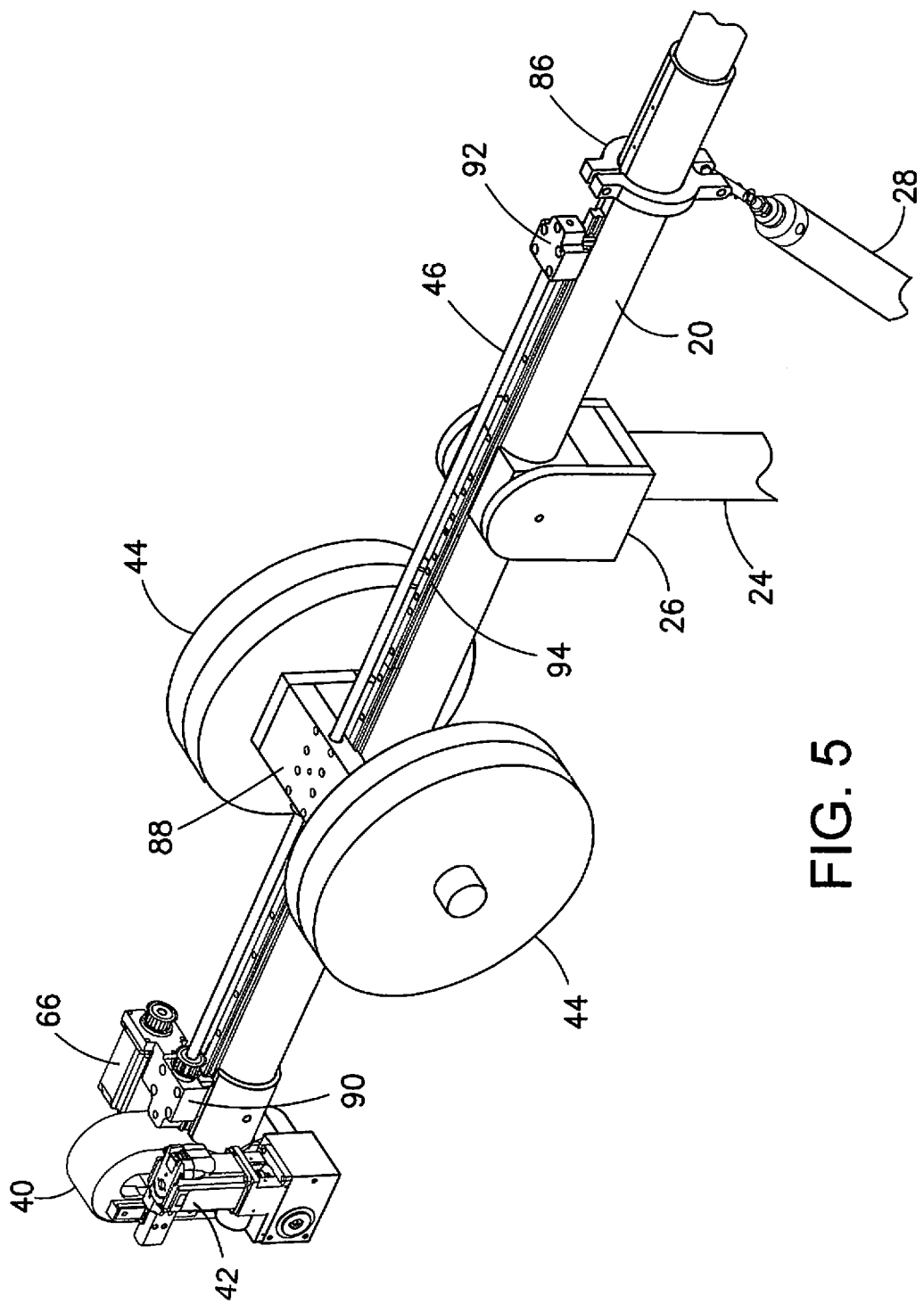
FIG. 5 is a diagram representing an isometric view of a subassembly comprising a portion of a boom arm and various components coupled thereto (including portions of a gimbal and a fall arrest damper), which subassembly is incorporated in the mobile boom system depicted in FIG. 4.
Figure 6:
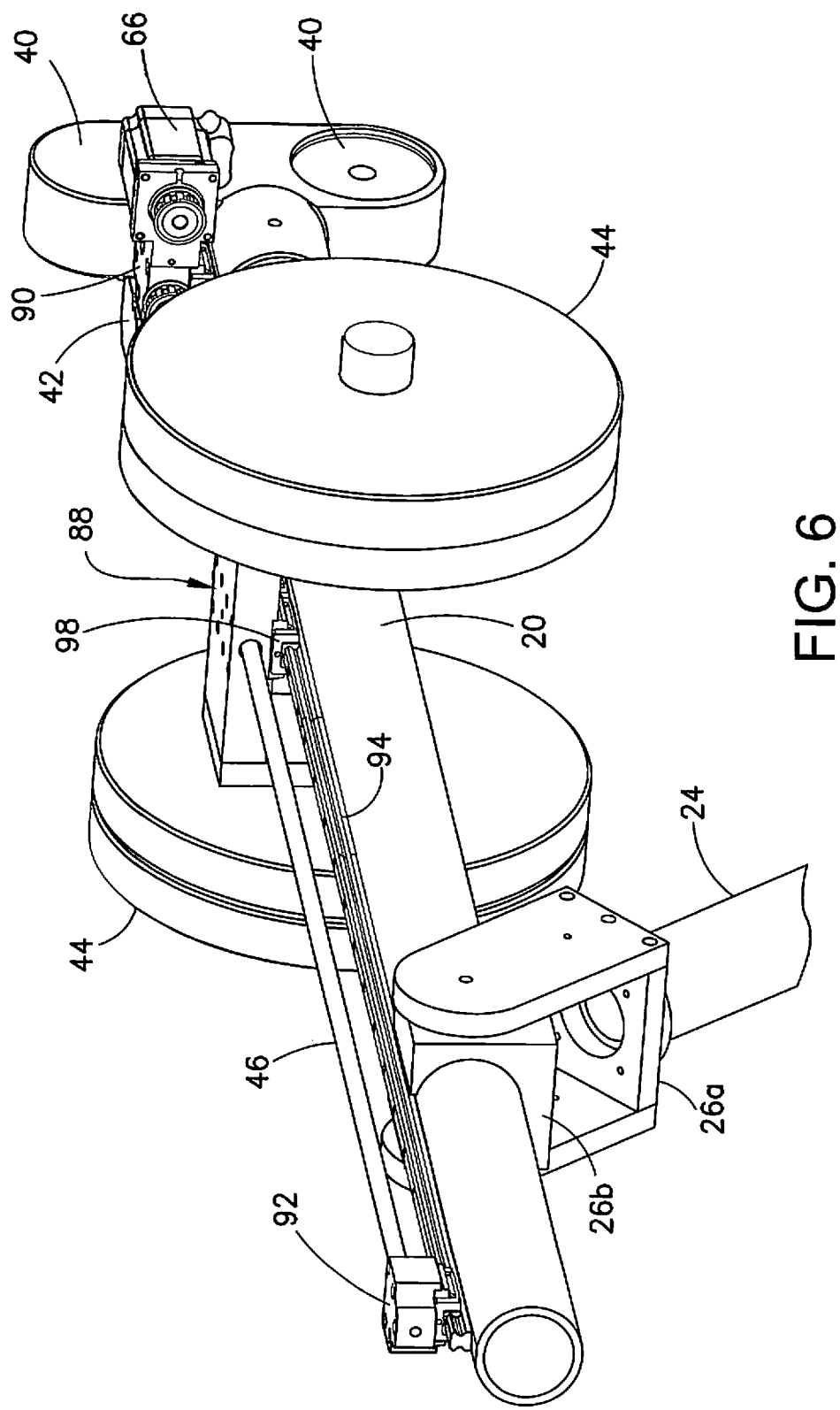
FIG. 6 is a diagram representing an isometric view of the subassembly depicted in FIG. 5 (except for the fall arrest damper) seen from an alternative vantage point.

As seen in FIG. 5, respective sets of counterweights 44 are carried by the counterweight carriage 88, which is moved along the boom arm 20 by the lead screw 46. The opposing ends of lead screw 46 are supported by respective bearings 90 and 92. Rotation of the lead screw 46 is driven by a counterweight motor 66 via a belt (not shown) which circulates on respective pulleys. The counterweight motor 66 is mounted to the proximal end of boom arm 20.

As best seen in FIG. 5, the counterweight carriage 88 travels along the boom arm 20 by means of a linear guide unit comprising a linear guide track 94 attached to the boom arm 20 and a slider 98 attached to the counterweight carriage 88. The slider 98 comprises a pair of recirculating ball bearings, the balls of which roll along the linear guide track 94. Optionally, the position of the counterweight carriage 88 can be measured by a position sensor (e.g., an encoder) to provide feedback to a counterweight motion control subsystem (which controls the counterweight motor 66). The gimbal comprises a gimbal part 26a attached to the rotary mast 24 and a gimbal part 26b attached to the boom arm 20, which gimbal parts are rotatable relative to each other about the boom arm tilt axis.

Figure 6A:
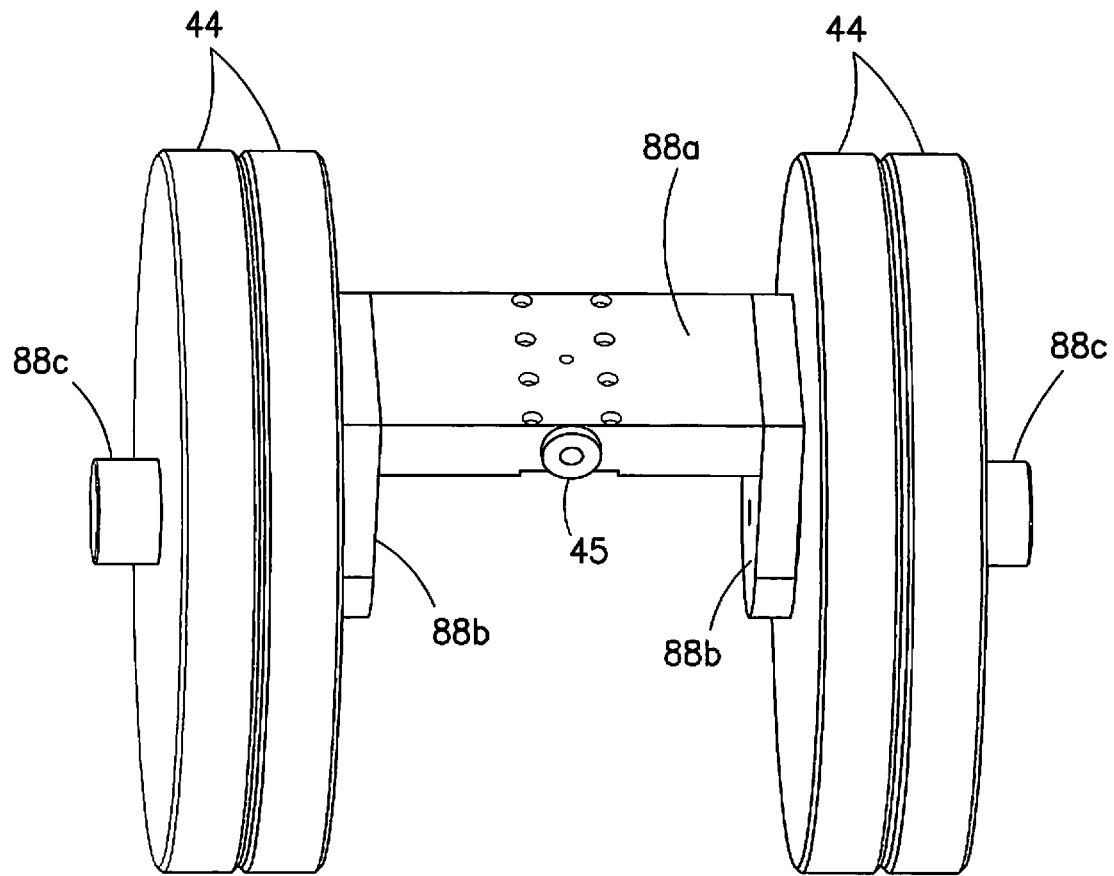
FIG. 6A is a diagram representing an isometric view of a counterweight/carriage assembly in accordance with one embodiment.

In accordance with the embodiment shown in FIG. 6A, the counterweight carriage 88 comprises a crosspiece 88a which is attached to the aforementioned slider 98 (not shown in FIG. 6A). The counterweight carriage 88 further comprises a pair of arms 88b attached to opposite ends of crosspiece 88a, and a pair of support rods 88c which project horizontally and outwardly from arms 88b respectively. In the example shown in FIG. 6A, each support rod 88c supports a respective pair of counterweights 44 in the form of disks. In addition, a nut 45 is installed in an opening in crosspiece 88a. The nut 45 threadably engages the lead screw 46 (not shown in FIG. 6A).

Figure 7:
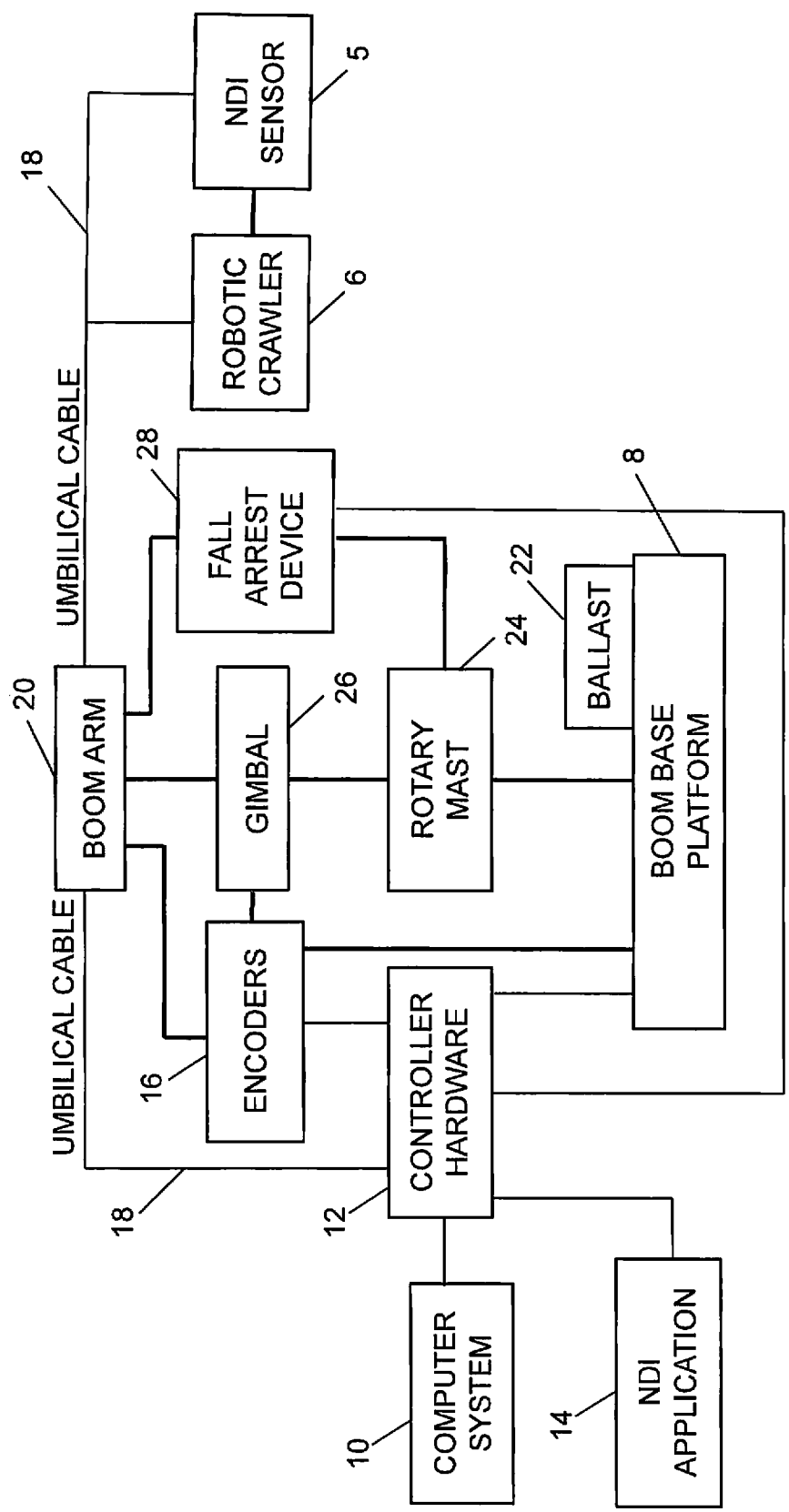
FIG. 7 is a block diagram showing connections between selected components of a system in accordance with one embodiment.

FIG. 7 is a block diagram showing mechanical and electrical connections between selected components of a system in accordance with one embodiment. The mechanical connections are indicated by boldface line segments between blocks. As depicted in FIG. 7, the boom base platform 8 carries ballast 22 and a support mast 24 (it may optionally also carry a tension reel, as shown in FIG. 1). The boom arm 20 is mounted to the rotary mast 24 via a gimbal 26. A robotic crawler 6, carrying a non-destructive inspection (NDI) sensor 5, is connected to one end of an umbilical cable 18 which passes through the hollow center of the boom arm 20. A fall arrest device 28 is provided for damping downward motion of the distal end of boom arm 20 in the event that the robotic crawler 6 falls off of the object (not shown) which is being inspected (e.g., a fuselage of an aircraft).

The mechanical movements of various components can be measured using encoders 16. The encoder pulses are received by controller hardware 12 (which is part of the electrical subsystem 50 indicated in FIG. 1). For example, encoders 16 may be provided for measuring the pan and tilt angles of the gimbal 26, the rotations of the wheels of the boom base platform 8, and the position of the counterweights 44 along the boom arm 20. In addition, the umbilical cable 18 includes electrical lines connecting the NDI sensor 5 and the robotic crawler 6 to controller hardware 12. The NDI sensor 5 may comprise an array of ultrasonic transducers for inspecting the surface on which the robotic crawler travels. In alternative embodiments, the robotic crawler may carry other types of tools, such as tools needed in maintenance or painting operations.

Still referring to FIG. 7, the motion control system comprises an onboard computer 10 programmed with motion control application software. The controller hardware 12 contains the system power supplies, relays, and data acquisition devices, integrates all the NDI sensor control connections, and provides an interface between the computer system 10 and the multi-function boom system and an interface between the computer system 10 and the robotic crawler 6. The computer 10 may comprise a general-purpose computer programmed with motion control application software comprising respective software modules for controlling the motors of the multi-function boom system and the robotic crawler.

For the NDI embodiment depicted in FIG. 7, the control system further comprises a ground-based computer 14 programmed with NDI scan application software. The ground-based computer 14 may be connected by the controller hardware by an electrical cable. The computer 14 hosts ultrasonic data acquisition and display software that controls the ultrasonic pulser/receiver unit (not shown) which sends pulses to and receives return signals from the NDI sensor 5 via the umbilical cable 18. The NDI scan application software controls all details of the scan data and the display of data.

The motion control application software on computer 10 also enables control of the cable motor of the onboard cable management system. The cable management system automatically feeds out the umbilical cable 18 or pulls in the slack as the robotic crawler 6 moves. As previously described with reference to FIG. 1, the cable management system comprises a pair of pinch rollers 40, driven by a cable motor 42, that grip the umbilical cable 18. The cable motor 42 is under the control of computer 10 programmed with motion control software which synchronizes the extension/retraction of the umbilical cable 18 with the movement of the boom base platform 8, extending or retracting the umbilical cable 18 as appropriate.

Figure 10:
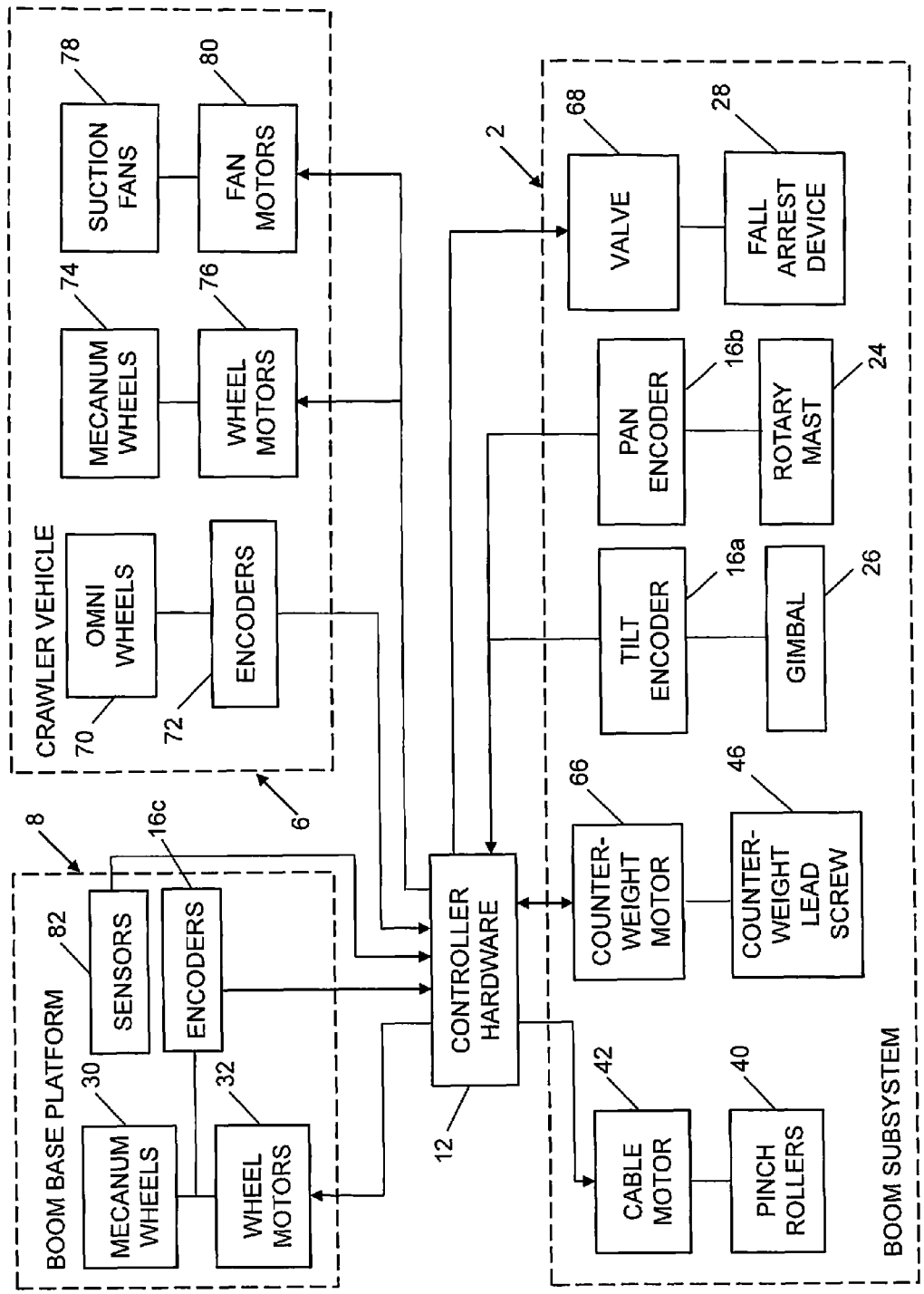
FIG. 10 is a block diagram showing connections between further components of the automated mobile boom system depicted in FIG. 7.

FIG. 10 is a block diagram showing connections between additional components of the automated mobile boom system depicted in FIG. 7. In accordance with the embodiment depicted in FIG. 10, the robotic crawler comprises a set of four omni wheels 70 for tracking vehicle motion and a set of four Mecanum wheels 74 for driving the robotic crawler 6 under the control of a computer. The controller hardware 12 comprising circuitry for supplying power and motor control signals to a plurality of stepper motors 76 which drive rotation of the Mecanum wheels 74 and to a plurality of fan motors 80 which drive rotation of a plurality of suction fans 78 that create suction in corresponding suction zones, as taught in U.S. Pat. No. 8,738,226. These independently controlled suction zones allow the system to control the amount of force exerted on the Mecanum wheels 74 by the contacting surface. In addition, while the Mecanum-wheeled robotic crawler 6 is being driven to move over a surface to be scanned, rotational encoders 72 coupled to the omni wheels 70 provide encoder pulses indicating incremental changes to the X, Y position of the robotic crawler 6. The controller hardware 12 further comprises a data acquisition device for recording counts of the encoder pulses, which counts are used by computer 10 (see FIG. 7) to track the vehicle motion in the manner described in U.S. Patent Application Publ. No. 2014/0278221.

Still referring to FIG. 10, the controller hardware 12 also supplies power and motor control signals to a plurality of stepper motors 32 which drive rotation of the Mecanum wheels 30 of the boom base platform 8. Incremental changes in the angular positions of the output shafts of stepper motors 32 may be indicated by encoder pulses output by respective encoders 16c to controller hardware 12. The encoders 16c may be internal to the stepper motors 32. In addition, a multiplicity of sensors 82 are provided around the perimeter of the boom base platform 8 to detect obstacles for the purpose of collision avoidance. The outputs of encoders 16c and sensors 82 are recorded by one of the multiple data acquisition devices incorporated as parts of the controller hardware 12.

The controller hardware 12 further comprises circuitry for providing power and control signals to the cable motor 42, which drives rotation of the cable pinch rollers 40, and to the counterweight motor 66, which drives rotation of the counterweight lead screw 46. The controller hardware 12 also comprises a data acquisition device for receiving data from a tilt angle sensor 16a and a pan angle sensor 16b. As previously mentioned, these angle sensors may take the form of rotational encoders, one mounted on gimbal part 26a shown in FIG. 6 and the other mounted in mast base 25 shown in FIG. 9. The aforementioned data acquisition device counts the number of encoder pulses output by angle sensors 16a and 16b. In addition, the controller hardware comprises circuitry for closing an electrically controlled valve 68 in response to a detected robotic crawler fall event, thereby enabling the fall arrest device 28 as previously described.

Base Platform Roll-Axis Pivot

One of the problems with four-wheeled vehicles traveling over non-planar surfaces is that the wheels can lift off the surface if the wheel axles are rigidly mounted to the frame. This is especially problematic for Mecanum-wheeled holonomic-motion vehicles, since these types of vehicles require all four wheels to maintain contact with the surface in order to have surface traction to be able to maintain full control of the motion. The system disclosed herein addresses this problem by using a roll-axis pivot rod 36 between the sub-platforms 52 and 54, as shown in FIG. 8. This simple feature allows a vehicle having four Mecanum wheels 30 (or four omnidirectional wheels) to maneuver asymmetrically over obstacles. In the embodiment depicted in FIG. 8, the roll-axis pivot rod 36 is supported by respective pairs of bearings 60 mounted to the respective sub-platforms 52, 54.

In addition, a modification to minimize yaw-axis twisting can be incorporated in the boom base platform 8. In the basic roll-axis pivot concept, when the boom base platform 8 encounters an obstacle that produces an asymmetrical force, such as when one of the Mecanum wheels 30 comes into contact with an obstacle, the force produced at that Mecanum wheel is not balanced by an equivalent force on the opposite Mecanum wheel. This results in a yaw-axis twisting torque (indicated by a curved arrow in FIG. 8) that bends the roll-axis pivot rod 36 elastically. Because the boom base platform 8 is rectangular, this yaw-axis twisting torque causes the outer edges of the sub-platforms 52 and 54 to bend toward each other. In the case where large asymmetric forces on the Mecanum wheels 30 are present, the edges of sub-platforms 52, 54 may come into contact and cause binding. This yaw-axis twisting problem can be solved by installing a pair of yaw-axis twist reduction rollers 56 and 58 having axles perpendicular to the roll and yaw axes, as shown in FIG. 8. The yaw-axis twist reduction rollers 56, 58 are disposed on opposing sides of the roll-axis pivot rod 36. In the embodiment depicted in FIG. 8, both yaw-axis twist reduction rollers 56, 58 are rotatably coupled to sub-platform 54 and bear against sub-platform 52 to maintain sub-platform separation. In the alternative, both yaw-axis twist reduction rollers 56, 58 can be rotatably coupled to sub-platform 52 or one yaw-axis twist reduction roller can be rotatably coupled to one sub-platform while the other yaw-axis twist reduction roller is rotatably coupled to the other sub-platform.

Figure 9:
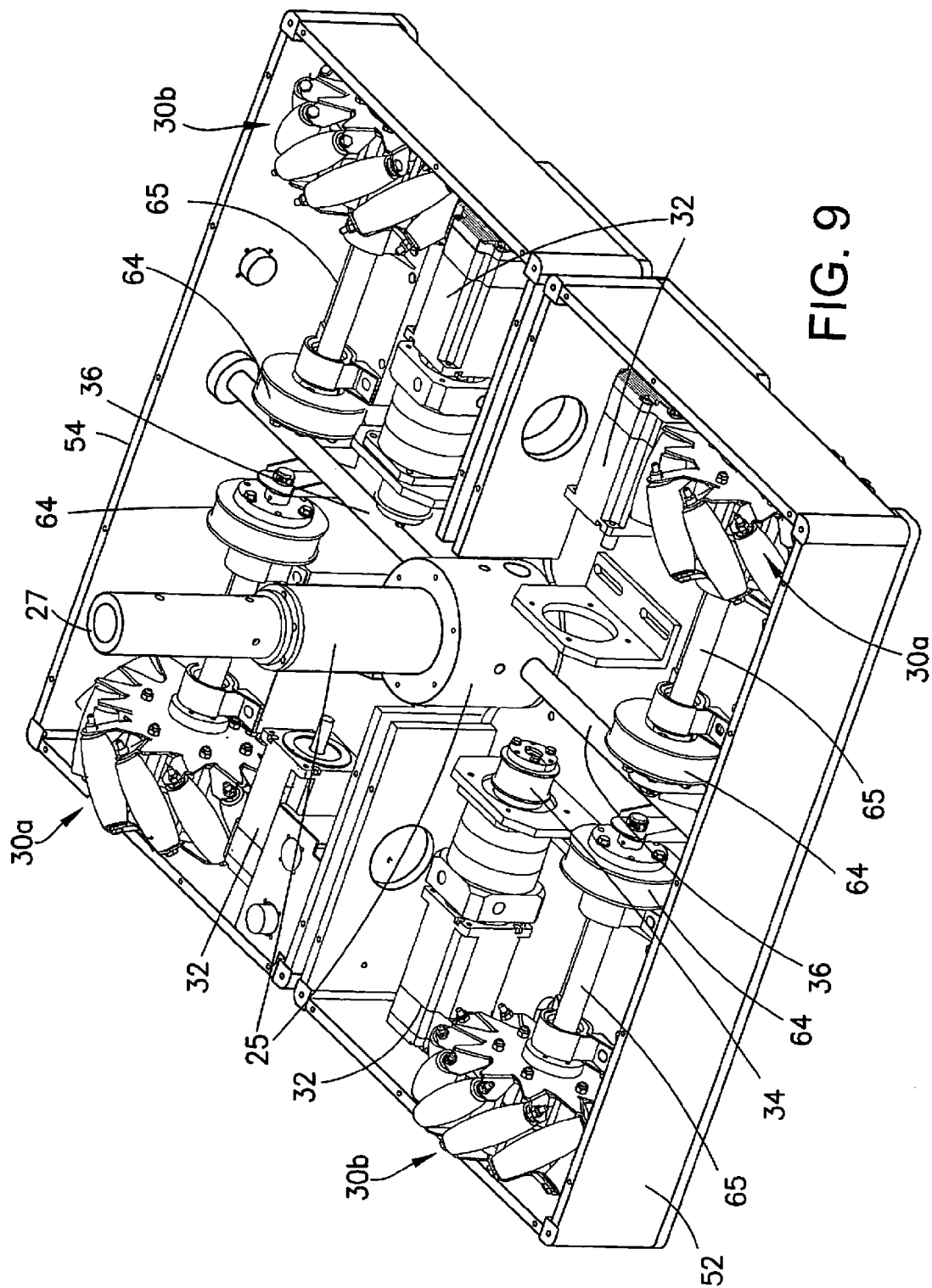
FIG. 9 is a diagram representing an isometric view (from a vantage point above) showing additional components of the holonomic-motion boom base platform depicted in FIG. 2.

FIG. 9 is a diagram representing an isometric view (from a vantage point above) showing additional components of the holonomic-motion boom base platform 8 depicted in FIG. 2. As seen in FIG. 9, each Mecanum wheel 30a or 30b is mechanically coupled to a respective pulley 64 by a respective axle 65, while the output shaft of each stepper motor 32 is mechanically coupled to a respective pulley 34. Each pulley 64 is coupled to a respective pulley 34 by a respective pulley belt (not shown), thereby enabling the stepper motors to independently drive rotation of respective Mecanum wheels.

In the embodiment depicted in FIG. 9, the mast base 25 is attached to sub-platform 54. The mast base 25 receives a mast rotor 27 to which the rotary mast 24 (shown in FIG. 1) is attached. The mast rotor 27 extends through the mast base 25 and is mounted on radial ball bearings (not shown) that allow rotation relative to the mast base 25. Additionally, the mast rotor has an encoder (not shown in FIG. 9, but see pan encoder 16b in FIG. 10) attached to track rotation of the rotary mast/boom arm about the pan axis.

As seen in FIG. 2, the mast base 25 has a diametral through-hole 99. Returning to FIG. 9, that diametral through-hole receives a roll-axis pivot rod 36 in the form of a circular cylindrical metal rod. The roll-axis pivot rod 36 is fixed to the rotary base 25. Since the rotary base 25 is fixed relative sub-platform 54, the roll-axis pivot rod 36 is also fixed relative to sub-platform 54. However, sub-platform 52 has two bearings (not shown) along the roll-axis pivot rod 36 which allow sub-platform 52 to rotate about the roll axis.

Base Platform Motion Control

The above-described mechanical apparatus moves under the control of the onboard computer 10 (see FIG. 7), which is programmed with motion control application software (hereinafter "motion controller"). The automated motion control scheme for the holonomic-motion base platform 8 is designed to operate in any one of a plurality of modes depending on circumstances. The primary goal of the base motion controller is to make sure that it holds the end of the boom arm with the umbilical cable above the robotic crawler without the boom base platform 8 (see FIG. 1) running into anything.

The multiple base platform motion modes may include one or more of the following: (1) a path following mode in which the computer controls the motion of the boom base platform to match the motion path of the robotic crawler; (2) a reactive mode in which the computer controls the motion of the boom base platform based on pan and tilt angles of the boom arm; and (3) collision avoidance in which the computer receives feedback from a multiplicity of sensors 82 mounted around the perimeter of the boom base platform 8 (see FIG. 10) and controls the boom base platform motion in a way that avoids a collision when an obstacle is detected.

Path Following Mode:

The path following mode uses the existing motion plan defined for the robotic crawler and converts the crawler motion coordinates (defined for operation on the surface of the target object) into the appropriate motion for the boom base platform moving on the floor or ground. One of the requirements for this type of motion control is to have real-time tracking of the robotic crawler and the boom base platform. This would be the preferred solution if a real-time tracking system, such as motion capture, was already available for crawler control. The steps of a motion capture process are shown in detail in the flow diagram of FIG. 11.

Figure 11:
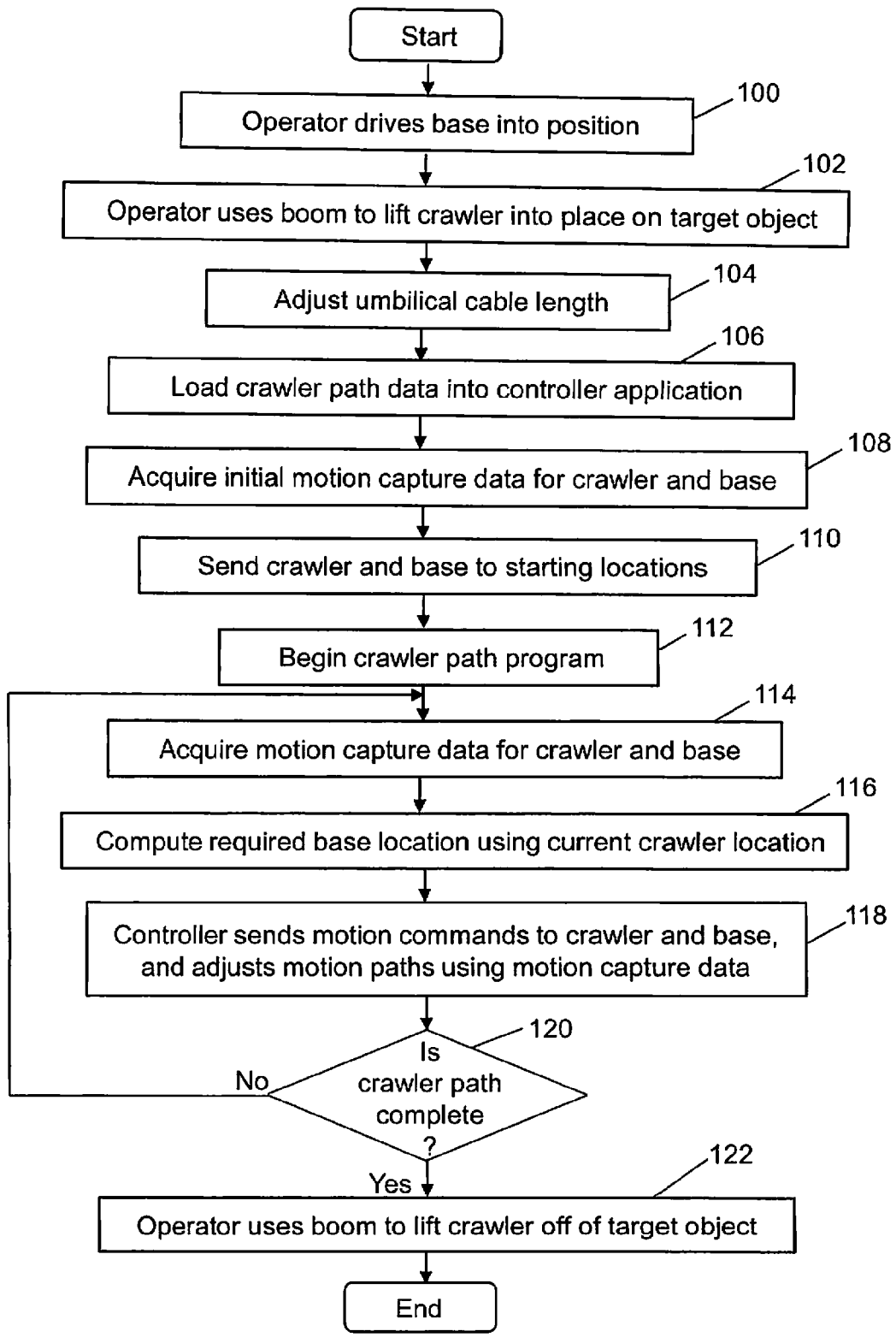
FIG. 11 is a process flowchart for an automated mobile boom system that uses motion capture-based tracking.

Referring to FIG. 11, first the operator drives the boom base platform into position (step 100). Then the operator uses the boom subsystem to lift the robotic crawler into place on the target object (step 102). Next, the operator adjusts the length of the portion of the umbilical cable extending from the robotic crawler to the distal end of the boom arm to provide a desired amount of slack (step 104). Then the operator loads a crawler motion path program for execution by the motion controller (step 106). This crawler motion path program may take the form of a specific motion script file that contains the parameters associated with a specific path to be followed by the crawler in order to perform a desired scanning operation. A motion capture system (or other motion tracking system) can then be activated to acquire data representing the respective initial positions of the robotic crawler and the boom base platform (step 108). In the case where motion capture is used, the crawler and the boom base platform may carry retro-reflective optical targets, which can be used to track their respective locations. The motion controller then controls the motorized Mecanum wheels to send the robotic crawler and the boom base platform to their respective starting locations (step 110). Next, the motion controller starts to execute the crawler motion path program (step 112). As the crawler moves over the surface of the target object, the motion controller acquires motion capture data for both the crawler and the boom base platform (step 114). The motion controller computes the required location of the boom base platform using the current crawler location (step 116). Then the motion controller send commands to the motors on the crawler and boom base platform to adjust their respective motion paths using the motion capture data (step 118). The motion controller monitors the current location of the crawler and determines whether it matches a final location corresponding to the end of the loaded crawler motion path (step 120). If the crawler motion path has not been completed, the process returns to step 114. If the crawler motion path has been completed, the scanning process is terminated and the operator uses the boom subsystem to lift the crawler off of the target object (step 122). For example, the crawler can be lifted by retracting the umbilical cable or by tilting the distal end of the boom arm upward. At the point in time when the cable has no slack, the suction fans of the crawler can be de-activated to release the crawler from the surface of the target object.

In order for motion of the boom base platform on the ground to match the motion of the crawler on the target object, the motion path data for the crawler needs to be projected onto the ground surface to compensate for the potential differences in orientation. This process uses transformation matrices of the current crawler location and the base location (both defined relative to the target object origin) to compute the offset transformation matrix describing the base location relative to the crawler location. This offset transformation matrix multiplies the path position data for the crawler to produce the required base position data defined on the ground surface.

Reactive Motion Control Mode:

As an alternative to the path following mode, the motion controller has a control mode in which the boom base platform reacts to position sensor data. This reactive mode does not require real-time absolute coordinate tracking of the crawler or boom base platform. Instead, this mode uses the on-board boom-angle sensors (i.e., tilt angle sensor 16*a* and pan angle sensor 16*b* identified in FIG. 8) to determine the position of the crawler relative to the boom base platform and feeds that data to the motion controller, which is programmed to maintain the boom pan and tilt angles in respective specific ranges. As the crawler moves to a location whereat the umbilical cable has no slack, further motion in the same direction will pull the umbilical cable, which in turn moves the boom arm and changes its pan and tilt angles.

The simplest form for implementing the base platform-following-crawler concept is a reactive mode in which only the boom pan angle is needed. This method makes an assumption about the location of the crawler relative to the distal end of the boom arm (for the basic case, that the crawler is vertically aligned with the end of the boom). This mode only requires that the operator set the initial starting orientation angle of the boom arm relative to the crawler. Then when the crawler is moving, the boom arm is pulled by the umbilical cable and causes the pan angle to change, which may cause the pan angle to exceed the specified deviation from the initial pan angle value. In response to the pan angle exceeding the specified limit, the boom base platform moves perpendicular to the initial pan angle to reduce the current pan angle, which in turn causes the current pan angle to return to the specified range.

Figure 12:
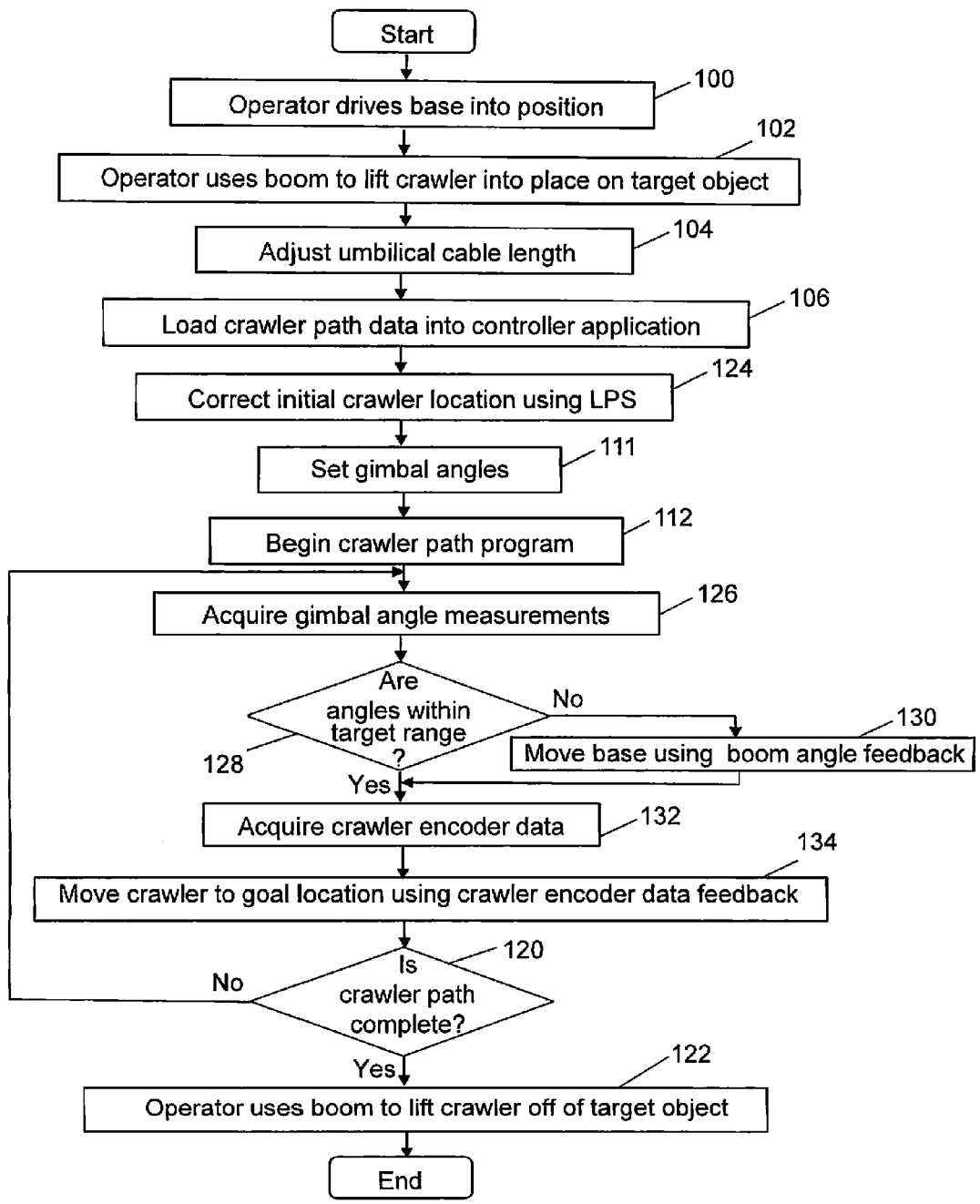
FIG. 12 is a process flowchart for an automated mobile boom system that uses relative tracking with gimbal angle feedback.

In accordance with one embodiment, the motion controller is programmed to react to the robotic crawler pulling on the umbilical cable by moving in the direction of the pull, which reduces the tension on the umbilical cable. In this system, the boom angle data is sent to the motion controller, which moves the boom base platform to return the pan angle, during horizontal movement of the crawler, back to the specified range. This self-contained feedback control method for the boom base platform operates independently of the crawler motion control, and is useful in conjunction with either automated control of the crawler or manual (e.g., teleoperated) crawler control. FIG. 12 shows the process flow for this method when a local positioning system (LPS) is used for location tracking.

Referring to FIG. 12, steps 100, 102, 104, and 106 are the same as those previously described with reference to FIG. 11. Optionally, the initial crawler location is corrected using the LPS (step 124). The target gimbal angles are set (step 111). Then the motion controller starts to execute the crawler motion path program (step 112). As the crawler moves over the surface of the target object, the motion controller acquires boom pan and tilt angle measurements from the angle sensors (step 126). The motion controller then determines whether the current pan and tilt angles are within their respective target ranges (step 128). If a current pan or tilt angle is not within its respective target range, the motion controller controls the motorized Mecanum wheels of the boom base platform to move the latter to a desired location where the pan and tilt angles are both within their respective target ranges (step 130). If the motion controller determines in step 128 that the pan and tilt angles are both within their respective target ranges, then the motion controller does not activate the boom base platform to move. (Although in the disclosed embodiments, the motion controllers for the crawler and the base are integrated, it is possible that these functions could be in two separate controllers.) In either case, before and after (and possibly during) the boom base platform movement, the motion controller also controls the motion of the robotic crawler by acquiring crawler encoder data (step 132) and then moving the crawler to a goal location in dependence on the crawler encoder data feedback (step 134). In addition, the motion controller monitors the current location of the crawler and determines whether it matches a final location corresponding to the end of the loaded crawler motion path (step 120). If the crawler motion path has not been completed, the process returns to step 126. If the crawler motion path has been completed, the scanning process is terminated and the operator uses the boom subsystem to lift the crawler off of the target object (step 122).

Collision Avoidance:

In accordance with the embodiment depicted in part in FIG. 10, a multiplicity of sensors 82 are mounted around the periphery of the boom base platform 8 to indicate the presence of obstacles in that specific region of the vehicle. The motion controller uses that sensor data to block additional motion from occurring in the direction associated with that particular sensor, but motion in the other directions is still allowed. Potential sensors include contact sensors, thru-beam sensors, and proximity sensors.

Usage Scenarios and Implementation Issues

At the beginning of the inspection task, the operator drives (teleoperates) the boom base platform 8 (see FIG. 1) to get it close to the target object 4; then the boom arm 20 is used as a crane to place the robotic crawler 6 on the surface of the target object. This task is performed by an operator who manually rotates the boom arm 20 to place the robotic crawler 6 at the desired location with its wheels in contact with the surface of the target object, after which the motorized cable extension/retraction subsystem is adjusted to provide the required amount of cable slack, while the motorized counterweight subsystem (comprising counterweights 44 and lead screw 46) is used to properly balance the boom arm 20. Angular motion feedback from the gimbal angle sensors (e.g., rotational encoders) is used by the boom arm control system to maintain the required offset distance (i.e., the distance from the robotic crawler to the floor) and to trigger a fall arrest response, if necessary. At the end of the inspection, the operator again uses the boom arm 20 as a crane to lift the robotic crawler 6 off the target object 4.

If the location of the crawler is known (in addition to the gimbal angle data), then advanced control is possible, such as adjusting the slack in the umbilical cable. In this more advanced mode, the location of the crawler is determined by additional sensors that are not part of the boom system (such as omni-wheel encoders on the crawler or motion capture tracking of the crawler). The slack in the umbilical cable could be adjusted based on the tilt angle of the boom arm. In general, letting out more slack increases the tilt angle and pulling in the slack decreases the tilt angle, but the controlling the tilt angle alone is not sufficient for all conditions. There are other factors that may also effect the tilt angle, so this part is not as clear-cut as motion control based on the pan angle. In order to use the tilt angle properly, additional information would need to be known, such as information about the surface geometry on which the crawler moves and/or the current path of the crawler.

In accordance with alternative embodiments disclosed herein, the motion of the mobile boom base platform is controlled to provide proper placement of the distal end of the boom arm 20 in close proximity to the location of the robotic crawler 6. This is done in such a way as to provide enough slack in the umbilical cable 18 to allow free movement of the robotic crawler 6, but not so much that the added weight of the umbilical cable 18 reduces the performance of the robotic crawler 6. In addition, reducing the amount of slack in the umbilical cable 18 is also beneficial in the case where the robotic crawler 6 slips off the surface and begins to fall; the shorter amount of slack reduces the time and fall speed that builds up before the boom arm fall response starts to resist the fall. In practice, three to five feet of umbilical cable 18 between the end of the boom arm 20 and the robotic crawler 6 may be sufficient to provide freedom of movement and reduce fall time. By knowing the locations of the robotic crawler 6 and boom base platform 8 and the pan and tilt angles, the proper amount of slack in the umbilical cable 18 can be continuously adjusted to maintain the proper offset. The cable slack may be controlled by a pinch-based roller subsystem similar to the one described in U.S. Pat. No. 9,010,684.

For short motion runs of the robotic crawler 6, the boom base platform 8 may not need to move. In this situation, all of the motion range needed is available from the boom arm 20 moving back and forth while the boom base platform 8 remains stationary. For longer motion runs of the robotic crawler 6, the range of motion of the boom arm 20 by itself is not sufficient, and in those cases the motors of the mobile boom system must be instructed to move to keep pace with the robotic crawler 6. As mentioned earlier, there are at least two ways that motion instructions for the boom base platform 8 can be generated automatically: (1) the direction and velocity of the holonomic-motion boom base platform 8 may be synchronized to that of the robotic crawler 6 so that the relative angular configuration of the boom arm 20 stays constant, based on location data from a tracking system; or (2) a reactive control mode can be used based on feedback from the sensors that measure the current pan and tilt angles of the boom arm 20 (without a separate tracking system).

In accordance with one embodiment, if a fall of the robotic crawler 6 were to occur, the measured angular velocity of the boom arm 20, as it tilts downward due to the added weight of the falling robotic crawler, would exceed the maximum allowable rate of rotation abut the tilt axis and the boom base platform 8 would be instructed to quickly respond by activating the electronically controlled fall arrest damper 28, which resists rotation of the boom arm 20 about the tilt axis to slow the rate of fall. During a fall, a large moment may be generated that could tip over the boom base platform 8—which is the reason why ballast may be required on the boom base platform 8. Water tanks that can be filled on-site may used to reduce the amount of ballast weight that needs to be shipped to the inspection site. Alternatively, metal plate-type weights may be used, as shown in FIG. 3.

In accordance with some embodiments, a collision avoidance system comprises a multiplicity of proximity sensors positioned on the perimeter of the boom base platform 8 is provided. This system would operate in a similar manner similar to what is described in U.S. Pat. No. 7,194,358, in which the platform vehicle motion is stopped in the direction indicated by the sensor detecting an obstacle but is still free to move in other directions. The collision detection sensors may be optical (e.g., IR reflection, thru-beam, laser, etc.), sonic/ultrasonic, and/or contact sensors. Depth cameras may also be used. This system can use used for unexpected obstacles, as well as planned stay-out zones. One possible use case to prevent the boom base platform 8 from moving into an area would be for the operator to place traffic cones (or similar items) around the inspection area to constrain the automated motion of the boom base platform 8.

Tracking of the boom base platform 8 and robotic crawler 6 is important to achieving one of the types of automated control of the system. This can be accomplished in several ways, such as using a system for motion capture tracking disclosed in U.S. Pat. No. 7,643,893, or a system for holonomic-motion omni-wheel-based object tracking disclosed in U.S. Patent Application Publ. No. 2014/0278221 combined with a system for absolute location correction disclosed in U.S. Pat. No. 9,043,146. For the other type of automated motion using boom angle data, external tracking is not required. At any point during the inspection, the boom base platform 8 may also be manually controlled (e.g., teleoperated with a joystick or other input device) in order to move the boom system into position.

In accordance with one embodiment, the system is portable and can be shipped to and from a remote inspection site. The boom subsystem 2 can be disassembled from the boom base platform 8 for shipping, and the boom base platform 8 itself can fit onto a standard wooden shipping pallet and driven on/off using a ramp.

In accordance with a lower-cost embodiment, the boom base platform would not be motorized. Such a system would retain the boom subsystem comprising a boom arm coupled to the boom base platform by means comprising a gimbal, a cable extension/retraction subsystem, controllable counterweights, and fall arrest elements, but would require the operator to push the boom base platform around manually.

The systems described above include one or more of the following specific features that differentiate this system other types of cable management systems: (1) The system can employ an overhead boom that follows the robotic crawler without requiring that the motion of the robotic crawler be stopped in order to reposition the cable management system. (2) The holonomic-motion boom base platform of this system allows movement in any direction without the motion constraints present with most other types of carts, trucks, or lift platforms. (3) The system eliminates the need to assign extra personnel on the ground for monitoring or moving the system, as is typically required for non-permanent fall protection systems. (4) The boom system eliminates the need for costly overhead superstructure for fall arrest of robotic crawlers. (5) Automated collision avoidance can be used with the control system to prevent collisions with the environment. (6) The system is portable. (7) When scaled for use with small crawling robots for aircraft fuselage/wing inspections, the system can be driven through doors (with the boom arm and rotary mast).

The cable management system disclosed herein seeks to address requirements for robotic crawler applications and includes automated feedback control to keep the umbilical cable optimally positioned while also providing fall protection and collision avoidance. The disclosed system is further advantageous because it does not involve use of permanent overhead structures or relatively large, semi-portable, overhead devices, which are not well suited for use around airplanes.

The boom-based cable management system disclosed above can be driven from its storage location out to an airplane in a depot or on a tarmac. The boom system automatically moves in the direction of the robotic crawler, such as in the direction of an airplane wing or fuselage, to keep the end of the boom arm over the robotic vehicle. The system can operate over large ranges of motion without constant human involvement.

The nature of this system described above makes it valuable for automated NDI in cases where crawling robots may be used to inspect a structure. This includes commercial airlines, military organizations, and other fields where NDI is done (nuclear, pipeline, energy, automotive, buildings, etc.). The system can be scaled up or down for use with larger or smaller types of robotic crawlers, which makes the system applicable for a wide range of application scenarios.

Several variations of this system are possible, such as the solution without the motorized base that was mentioned earlier as a low-cost option. More elaborate setups to address larger systems are also possible, such as synchronizing multiple holonomic-motion base platforms working together. The techniques disclosed herein can be applied well beyond the aerospace industry, to robotic work spaces above the ground where fall protection is needed.

While mobile cable management systems have been described with reference to various embodiments, it will be understood by those skilled in the art that various changes may be made and equivalents may be substituted for elements thereof without departing from the scope of the claims set forth hereinafter. In addition, many modifications may be made to adapt the concepts and reductions to practice disclosed herein to a particular situation without departing from the scope of the claims.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices having a processing unit (e.g., a central processing unit) and some form of memory (i.e., computer-readable medium) for storing a program which is readable by the processing unit. For example, a computer system may comprise respective processors incorporated in a plurality of devices and a control computer in communication with those processors.

The method claims set forth hereinafter should not be construed to require that the steps recited therein be performed in alphabetical order (any alphabetical ordering in the claims is used solely for the purpose of referencing previously recited steps) or in the order in which they are recited. Nor should they be construed to exclude any portions of two or more steps being performed concurrently or alternatingly.

The invention claimed is:

1. A mobile boom system comprising:
a self-propellable mobile boom base platform comprising a plurality of rolling elements and a plurality of motors respectively coupled to said plurality of rolling elements;
a rotary mast carried by said boom base platform and rotatable relative to said boom base platform about a pan axis;
a gimbal comprising a first portion attached to said rotary mast and a second portion rotatable relative to said rotary mast about a tilt axis;
a hollow boom arm having first and second ends and an intermediate portion coupled to said gimbal;
a cable extending through said hollow boom arm;
a pan angle sensor for detecting a pan angle of said boom arm; and
a computer system programmed to receive pan angle data from said pan angle sensor and send control signals to said motors for changing the position of said boom base platform as a function of at least said pan angle data.

2. The mobile boom system as recited in claim 1, wherein said computer system is programmed to cause said boom base platform to move when the pan angle of said boom arm reaches a specified threshold pan angle.

3. The system as recited in claim 1, further comprising a tilt angle sensor for detecting a tilt angle of said boom arm, wherein said computer system is further programmed to receive tilt angle data from said tilt angle sensor and send control signals to said motors for changing the position of said boom base platform as a function of said pan angle data and said tilt angle data.

4. The system as recited in claim 3, further comprising a multiplicity of sensors positioned on a perimeter of the boom base platform, wherein said computer system is further programmed to receive data from said sensors and send control signals to said motors for changing the position of said boom base platform as a function of said pan angle data and said tilt angle data except in directions associated with any of said sensors which are outputting data indicating obstacles in said directions.

5. The system as recited in claim 1, further comprising a robotic crawler attached to a distal end of said cable, said computer system being further programmed to control movement of said robotic crawler on a surface by means of signals communicated to said robotic crawler via said cable.

6. The system as recited in claim 1, wherein said boom base platform comprises:
a frame;
a plurality of wheels rotatably mounted to said frame, each wheel comprising a respective plurality of rollers having axes of rotation not parallel to an axis of rotation of said wheel; and
a plurality of motors equal in number to the number of wheels, each motor being operable to drive rotation of a respective one of said wheels.

7. The system as recited in claim 1, wherein said boom base platform comprises:
first and second sub-platforms;
first and second rolling elements rotatably coupled to said first sub-platform;
third and fourth rolling elements rotatably coupled to said second sub-platform; and
a roll-axis pivot rod comprising first and second portions respectively coupled to said first and second sub-platforms,
wherein at least one of said first and second sub-platforms is rotatably coupled to said roll-axis pivot rod.

8. The system as recited in claim 7, wherein said first through fourth rolling elements comprise first through fourth wheels respectively, further comprising first through fourth motors for respectively driving rotation of said first through fourth wheels.

9. A mobile boom system comprising:
a mobile boom base platform;
a rotary mast carried by said boom base platform and rotatable relative to said boom base platform about a pan axis;
a gimbal comprising a first portion attached to said rotary mast and a second portion rotatable relative to said rotary mast about a tilt axis;
a boom arm having first and second ends and an intermediate portion coupled to said gimbal;
a cable supported by said boom arm;
a robotic crawler attached to a distal end of said cable;
an electrically controlled boom arm fall arrest mechanism having first and second ends respectively coupled to said boom arm and said rotary mast;
a tilt angle sensor for detecting a tilt angle of the boom arm; and
a computer system programmed to monitor the output of said tilt angle sensor and issue a fall arrest trigger signal to said boom arm fall arrest mechanism in response to a rate of rotation of the boom arm about said tilt axis exceeding a specified threshold.

10. The system as recited in claim 9, wherein said boom arm fall arrest mechanism comprises:
a cylinder having one end attached to said rotary mast and a piston coupled to said boom arm or a strut attached to said boom arm; and
an electrically controlled valve,
wherein fluid inside said cylinder resists retraction of said piston when said valve is closed and does not resist retraction of said piston when said valve is open.

11. The system as recited in claim 9, wherein said boom arm fall arrest mechanism comprises:
an oil-filled cylinder attached to said rotary mast at a mount point; and
an oil reservoir attached to said rotary mast near the mount point of said oil-filled cylinder,
wherein said oil-filled cylinder is in fluid communication with said oil reservoir.

12. The system as recited in claim 9, further comprising:
at least one counterweight supported on a portion of the boom arm disposed between the intermediate portion and the first end; and
a counterweight positioning subsystem for changing the a position of the at least one counterweight relative to the gimbal,
wherein said computer system is further programmed to receive tilt angle data from the tilt angle sensor and send control signals to the counterweight positioning subsystem for controlling the position of the at least one counterweight in accordance with an automatic balancing algorithm based on feedback of tilt angle data from said tilt angle sensor.

13. The system as recited in claim 12, wherein said counterweight positioning subsystem comprises a motor-driven, non-backdrivable lead screw which holds said at least one counterweight in place even when power is disrupted.

14. A system comprising:
a holonomic-motion boom base platform;
a rotary mast carried by said boom base platform and rotatable relative to said boom base platform about a pan axis;
a boom arm supported by said boom base platform and rotatable relative to said boom base platform about a pan axis;
a cable supported by said boom arm and having a distal end;
a holonomic-motion robotic crawler attached to the distal end of said cable; and
a computer system programmed to control motion of said boom base platform to match a motion path of said robotic crawler.

15. The system as recited in claim 14, further comprising a real-time tracking system configured to acquire data representing a current location of said robotic crawler, wherein said computer system is further programmed to compute a target location of said boom base platform using the data representing the current location of said robotic crawler.

16. The system as recited in claim 15, wherein said computer is system is programmed to project motion path data for said robotic crawler onto a ground surface using an offset transformation matrix describing the location of said boom base platform relative to the location of said robotic crawler.

17. The system as recited in claim 14, wherein said computer system is further programmed to control movement of said robotic crawler on a surface by means of signals communicated to said robotic crawler via said cable.

18. The system as recited in claim 14, wherein said robotic crawler comprises a plurality of wheels and a plurality suction zones, each of said plurality of wheels comprising a respective plurality of rollers rotatably mounted along a circumference.

19. The system as recited in claim 14, wherein said boom base platform comprises:
first and second sub-platforms;
first and second wheels rotatably coupled to said first sub-platform;
third and fourth wheels rotatably coupled to said second sub-platform; and
a roll-axis pivot rod comprising first and second portions respectively coupled to said first and second sub-platforms,
wherein said first sub-platform is rotatably coupled to said roll-axis pivot rod, and each of said first through fourth wheels comprises a respective plurality of rollers rotatably mounted along a circumference.

20. The system as recited in claim 19, wherein said boom base platform further comprises first and second yaw-axis twist reduction rollers disposed on opposing sides of said roll-axis pivot rod, each of said first and second yaw-axis twist reduction rollers being rotatably coupled to one of said first and second sub-platforms and bearing against the other of said first and second sub-platforms.

\* \* \* \* \*